US011550969B2

(12) United States Patent
Mochizuki et al.

(10) Patent No.: US 11,550,969 B2
(45) Date of Patent: Jan. 10, 2023

(54) DEVICE, SYSTEM, METHOD AND PROGRAM FOR PRODUCING FRAGMENT MODEL

(71) Applicants: RIKKYO EDUCATIONAL CORPORATION, Tokyo (JP); MIZUHO RESEARCH & TECHNOLOGIES, LTD., Tokyo (JP)

(72) Inventors: Yuji Mochizuki, Tokyo (JP); Takayuki Tsukamoto, Tokyo (JP); Kaori Fukuzawa, Tokyo (JP)

(73) Assignees: RIKKYO EDUCATIONAL CORPORATION, Tokyo (JP); MIZUHO RESEARCH & TECHNOLOGIES, LTD., Tokyo (JP)

( * ) Notice: Subject to any disclaimer, the term of this patent is extended or adjusted under 35 U.S.C. 154(b) by 1505 days.

(21) Appl. No.: 14/442,321

(22) PCT Filed: Mar. 27, 2013

(86) PCT No.: PCT/JP2013/059120
§ 371 (c)(1),
(2) Date: May 12, 2015

(87) PCT Pub. No.: WO2014/076980
PCT Pub. Date: May 22, 2014

(65) Prior Publication Data
US 2016/0078155 A1 Mar. 17, 2016

(30) Foreign Application Priority Data
Nov. 16, 2012 (JP) .............................. JP2012-252456

(51) Int. Cl.
*G06F 30/20* (2020.01)
*G16B 15/00* (2019.01)
(Continued)

(52) U.S. Cl.
CPC ............. *G06F 30/20* (2020.01); *G16B 15/00* (2019.02); *C30B 29/66* (2013.01); *G06F 2111/10* (2020.01)

(58) Field of Classification Search
CPC ......... C30B 29/00; C30B 29/66; G06F 30/00; G06F 2111/10; G16B 15/00
See application file for complete search history.

(56) References Cited

FOREIGN PATENT DOCUMENTS

JP 2009-193552 A 8/2009
JP 2010-117986 A 5/2010
(Continued)

OTHER PUBLICATIONS

Nakano, Tatsuya, et al., "Development of the four-body corrected fragment molecular orbital (FMO4) method," *Chemical Physics Letters*, vol. 523, pp. 128-133 (2012).
(Continued)

*Primary Examiner* — Robert M Kunemund
(74) *Attorney, Agent, or Firm* — Christensen, Fonder, Dardi & Herbert PLLC

(57) ABSTRACT

A device for creating a fragment model from a crystal model is equipped with a division position identifying section adapted for identifying multiple division atom pairs for multiple atoms contained in the crystal model. The atoms in the division atom pairs are contained in different fragment models. The device is additionally equipped with a model creating section adapted for identifying each of multiple atom groups each composed of atoms bonded to each other in the crystal model and for creating fragment models respectively corresponding to the identified atom groups.

19 Claims, 13 Drawing Sheets

(51) Int. Cl.
  *G06F 111/10* (2020.01)
  *C30B 29/66* (2006.01)

(56) References Cited

FOREIGN PATENT DOCUMENTS

JP      5067682 B1    11/2012
JP      2013-101533 B1  5/2013

OTHER PUBLICATIONS

Nakano, Tatsuya, et al., "Application of Fragment Molecular Orbital (FMO) Method to Nano-Bio Field," *J. Comput. Chem. Jpn.*, vol. 6, No. 3, pp. 173-184 (2007).

Fukuzawa, Kaori, et al., "Applications of the Fragment Molecular Orbital Method for Bio-Macromolecules," *J. Comput. Chem. Jpn.*, vol. 6, No. 3, pp. 185-198 (2007).

Kato, Yuji, "FMO-ho ni Motozuku Kaikakukei Bunshi no Atsukai," *The 91st Annual Meeting of the Chemical Society of Japan in Spring Koen Yokoshu II*, p. 466 (Mar. 11, 2011).

Komeiji, Yuto, et al., "FMO-MD: ab initio Fragment Molecular Orbital-Based Molecular Dynamics Simulation," *Journal of the Japan Society of Simulation Technology*, vol. 29, No. 1, pp. 2-9 (Mar. 15, 2010).

Fujita, Takatoshi, et al., "Accuracy of fragmentation in ab initio calculations of hydrated sodium cation," *Chemical Physics Letters*, vol. 478, pp. 295-300 (2009).

Yoshioka, Akio, et al., "Prediction of probable mutations in influenza virus hemagglutinin protein based on large-scale ab initio fragment molecular orbital Calculations," *Journal of Molecular Graphics and Modelling*, vol. 30, pp. 110-119 (2011).

Hitaoka, Seiji, et al., "Correlation Analyses on Binding Affinity of Sialic Acid Analogues with Influenza Virus Neuraminidase-1 Using ab Initio MO Calculations on Their Complex Structures," *J. Chem. Inf. Model*, vol. 50, No. 10, pp. 1796-1805 (2010).

Fig.9

```
                                                          Vfrag
 N  Cfm       Na  Nb  nBDA  nBAA  Nc  Cnt  Fname
 1  Si1O3H2   6   44   1     1    0   10   Si1:0304-06H3H6
 2  Si1O3H2   6   44   1     1    0   10   Si2:030506-H3H5
 3  Si1O3H2   6   44   1     1    0    5   Si3:01-0205H2H5
 4  Si2O5H2   9   75   2     2    0   20   Si2:Si3:01-02030506-H2H3
 ⋮   ⋮        ⋮   ⋮    ⋮     ⋮    ⋮    ⋮    ⋮
```

Fig.10

```
                                                                  Veva
 Si3-02
 Si1-06     ← Dcand
 Si2-01
 Si1-04
 N  Cfm      Na   Nb   nBDA  nBAA  Nc   Cnt   Fname
 ⋮   ⋮       ⋮    ⋮     ⋮     ⋮    ⋮     ⋮     ⋮
 Absolute sum of charge 10                           ← Dresl
                          ↖ Pseq
 Si3-02
 Si1-06     ← Dcand
 Si2-01
 Si3-04
 N  Cfm      Na   Nb   nBDA  nBAA  Nc   Cnt   Fname
 ⋮   ⋮       ⋮    ⋮     ⋮     ⋮    ⋮     ⋮     ⋮
 Absolute sum of charge 10                           ← Dresl
                            ↖ Pseq
```

Fig.20

VMcon

| N |   |   | N |   |   |
|---|---|---|---|---|---|
| 2 | Si1 | – *, | 2 | O4 | – * |
| 3 | Si2 | – *, | 3 | O6 | – * |
| 7 | O1 | – *, | 7 | Si3 | – * |

Fig.21

VMeva

Model Data    SIO_UC_STEP1 ← Dif

| Nmtype | Comb | Ncs | Amax | Nbs |
|--------|------|-----|------|-----|
| 1 | 000 | 10 | 21 | 181 |
| 2 | 001 | 10 | 30 | 238 |
| 3 | 010 | 10 | 25 | 196 |
| 4 | 011 | 10 | 30 | 238 |
| 5 | 100 | 10 | 27 | 207 |
| 6 | 101 | 10 | 24 | 194 |
| 7 | 110 | 10 | 27 | 207 |
| 8 | 111 | 10 | 24 | 194 |

DEVICE, SYSTEM, METHOD AND PROGRAM FOR PRODUCING FRAGMENT MODEL

RELATED APPLICATIONS

The present is a National Phase entry of PCT Application No. PCT/JP2013/059120, filed Mar. 27, 2013, which claims priority from Japanese Patent Application No. 2012-252456, filed Nov. 16, 2012 the disclosures of which are hereby incorporated by reference herein in their entirety.

FIELD OF THE INVENTION

The present disclosure relates to a device, a system, a method, and a program for creating a fragment model.

BACKGROUND OF THE INVENTION

Calculation of an interaction energy by using a fragment molecular orbital method (FMO method) is used as one method for analyzing an interaction between a protein and a compound that acts as a ligand of the protein (for example, see Non-Patent Document 1, Non-Patent Document 2, and Non-Patent Document 3).

PRIOR ART DOCUMENTS

Non-Patent Documents

Non-Patent Document 1: Nakano, Mochizuki et al., Chem. Phys. Lett., 523, pp. 128-133 (2012)

Non-Patent Document 2: Nakano et al., J. Comput. Chem. Jpn., Vol. 6, No. 3, pp. 173-184 (2007)

Non-Patent Document 3: Fukuzawa et al., J. Comput. Chem. Jpn., Vol. 6, No. 3, pp. 185-198 (2007)

SUMMARY OF THE INVENTION

With the above FMO method, when a fragment model is created, a bond detached atom (BDA) and a bond attached atom (BAA), which forms a pair with the BDA, are set by a user for the model on which a calculation is made. That is, the respective paired BDA and BAA are included in different fragment models. The pair of BDA and BAA is called a divisional atom pair. Suitable setting of BDA and BAA improves accuracy of a calculated result obtained by the FMO method.

At this time, when a one-dimensional polymer model such as a protein is subject to the calculation, BDA candidates and BAA candidates are arranged one-dimensionally, and thus an error is unlikely to occur in the setting of BDA and BAA. However, when a nonmetallic crystal model such as low quartz is subject to the calculation, BDA candidates and BAA candidates scatter three-dimensionally and complicatedly, and thus errors are likely to occur in the setting of BDA and BAA compared to the case of the one-dimensional polymer model.

It is an objective of the present disclosure to provide a fragment model creating device, a fragment model creating system, a fragment model creating method, and a fragment model creating program that improve accuracy of setting of BDA and BAA at the creation of a fragment model.

In accordance with one aspect of the present invention, a fragment model creating device for creating a fragment model from a crystal model is provided. The fragment model creating device includes a division position identifying section and a model creating section. The division position identifying section is adapted for identifying a plurality of division atom pairs for a plurality of atoms included in the crystal model. The atoms in the division atom pairs are included in different fragment models. The model creating section is adapted for identifying each of a plurality of atom groups composed of atoms bonded to each other in the crystal model to create fragment models corresponding to the respective identified atom groups. Each of the fragment models is set as a corresponding basic divisional unit. Each of the atoms included in the crystal model is associated with any one of the atoms included in the basic divisional unit. The division position identifying section is adapted for setting candidates of the division atom pairs in the atoms included in the basic divisional units and identifying the candidates included in each basic divisional unit as the division atom pairs.

In accordance with another aspect of the present invention, a fragment model creating system is provided that includes an input device and a fragment model creating device for creating a fragment model by using data input from the input device. The fragment model creating device includes a division position identifying section and a model creating section. The division position identifying section is adapted for identifying a plurality of division atom pairs for a plurality of atoms included in a crystal model corresponding to the data input from the input device. The atoms in the division atom pairs are included in different fragment models. The model creating section is adapted for identifying a plurality of atom groups composed of atoms bonded to each other in the crystal model and creating fragment models corresponding to the identified atom groups. The fragment models are set as corresponding basic divisional units. Each of the atoms included in the crystal model is associated with any one of the atoms included in each of the basic divisional units. The division position identifying section is adapted for setting candidates of the division atom pairs in the atoms included in the basic divisional units and identifying the candidates included in the respective basic divisional units as the division atom pairs.

In accordance with a yet another aspect of the present invention, a fragment model creating method for creating a fragment model is provided. The method includes: identifying a plurality of division atom pairs for a plurality of atoms included in a crystal model, the atoms in the division atom pairs being included in different fragment models; and identifying each of a plurality of atom groups composed of atoms bonded to each other in the crystal model to create fragment models corresponding to the respective identified atom groups. Each of the fragment models is set as a corresponding basic divisional unit. Each of the atoms included in the crystal model is associated with any one of the atoms included in the basic divisional unit. The identification of the division atom pairs includes setting candidates of the division atom pairs in the atoms included in the basic divisional units and identifying the candidates included in each basic divisional units as the division atom pairs.

In accordance with a further aspect of the present invention, a non-transitory computer readable recording medium is provided that records therein a program for creating a fragment model by using a fragment model creating system having a controller for creating a fragment model. When the program is executed, the controller is caused to function as: a division position identifying section for identifying a plurality of division atom pairs for a plurality of atoms included in a crystal model, the atoms in the division atom pairs being included in different fragment models; and a model creating section for identifying each of a plurality of atom groups composed of atoms bonded to each other in the crystal model to create fragment models corresponding to the respective identified atom groups. Each of the fragment models is set as a corresponding basic divisional unit. Each of the atoms included in the crystal model is associated with any one of the atoms included in the basic divisional unit. The division position identifying section sets candidates of the division atom pairs in the atoms included in the basic divisional units and identifies the candidates included in each basic divisional unit as the division atom pairs.

BRIEF DESCRIPTION OF THE DRAWINGS

FIG. 9 is a diagram illustrating one example of a display view of a charge state list according to the first embodiment;

FIG. 10 is a diagram illustrating one example of a display view of an evaluation list according to the first embodiment;

FIG. 20 is a diagram illustrating one example of a display view of a merging condition in the second embodiment;

FIG. 21 is a diagram illustrating one example of a display view of a result of the merging process in the second embodiment.

DETAILED DESCRIPTION OF THE PREFERRED EMBODIMENTS

First Embodiment

A first embodiment will be described below with reference to FIGS. 1 to 16. A model of clusters cut out from crystal (hereinafter, a crystal model) and a basic divisional unit that are used for creating a fragment model will be described with reference to FIGS. 1 to 6. Examples of nonmetallic crystal to be the crystal model are covalent crystal such as diamond, boron nitride, silicon, silicon carbide, gallium, and gallium arsenide, or crystal having covalency and ion binding properties such as zeolite, quartz, titanium oxide, aluminum oxide, and zinc oxide. Further, the crystal model may include a point defect, a line defect, a plane defect, a step, which is a stepped portion, or a kink, which is a portion where a stagger for one atom occurs on a line of a step. Further, the target for the crystal model includes crystal in which some atoms are replaced by atoms different from bulk, and crystal to which atoms different from the bulk are added. Further, the target for the crystal model also includes mixed crystal of solid phase where two or more substances melt together. The mixed crystal includes interstitial mixed crystal where a gap of a space lattice of one substance have an atom of another substance, and substitutional mixed crystal where an atom on a specific position (lattice point) in the space lattice of one substance is substituted by an atom of another substance.

FIGS. 1 to 6 illustrate low quartz among the nonmetallic crystals as one example of the crystal model. Si and O that are constituent atoms of the crystal model are each indicated by a circle. Symbols of elements in the constituent atoms in the crystal model are shown according to each of the constituent atoms. Numbers for identifying the constituent atoms in a single crystal lattice are given to the symbols of elements.

Figure 1:
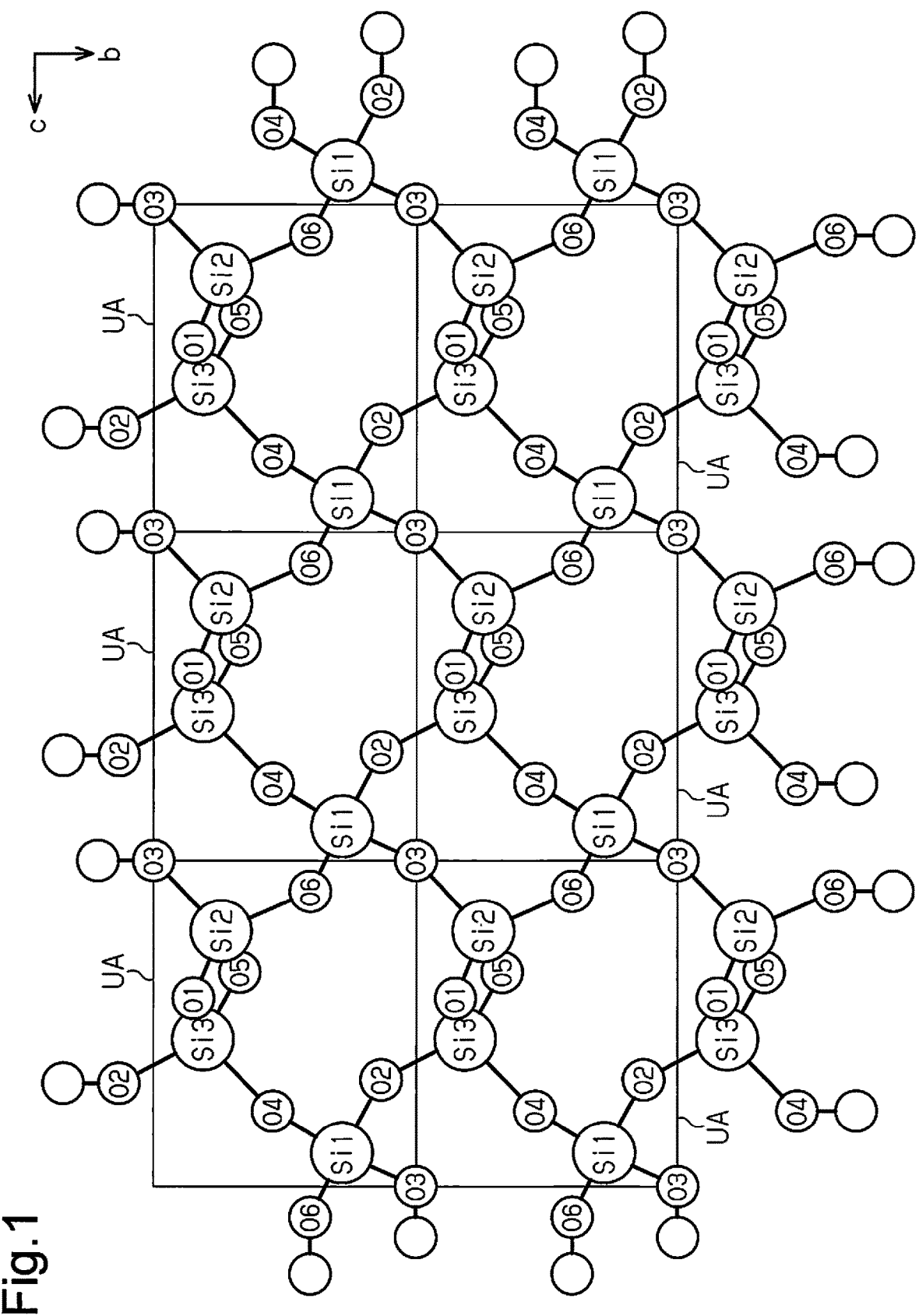
FIG. 1 is an a-axial projection view of low quartz for describing one example of a basic divisional unit in the present disclosure.

In an a-axial projection of a low quartz model shown in FIG. 1, a crystal lattice UA includes Si1, Si2 and Si3, which are three Si atoms, and O1, O2, O4, O5 and O6, which are five O atoms. The crystal lattice UA further includes four ¼ O3. Si1 is covalently bonded to O2, O3, O4, and O6. Si2 is covalently bonded to O1, O3, O5, and O6. Si3 is covalently bonded to O1, O2, O4, and O5. These covalently bonded atoms are connected by thick solid lines in FIG. 1.

The crystal lattice UA is a unit that characterizes symmetry of a crystal structure. Specific atoms in one crystal lattice UA constitute a part of another crystal lattice UA in some cases. For example, an O3 in the low quartz model is a constituent atom that is common in eight crystal lattices UA adjacent in three dimensions. Since ⅛ O3 is arranged at each of eight apexes in one crystal lattice UA, one crystal lattice UA includes collectively one O3.

In contrast, since a basic divisional unit for creating a fragment model is a unit that enables calculation of an electronic state, specific atoms constituting one basic divisional unit do not constitute another basic divisional unit. For example, the basic divisional unit in the low quartz model is constituted by Si1 to Si3, which are three Si atoms, and O1 to O6, which are six O atoms. O3 is included in any one of basic divisional units. As a result, the crystal model used for creating a fragment model is treated as an atom group composed of basic divisional unit aggregate in which basic divisional units are repeated. The basic divisional unit may be an atom group defined based on a plurality of atoms included in single crystal lattice UA, and may be also an atom group defined based on a plurality of atoms included in a plurality of crystal lattices UA.

Figure 2:
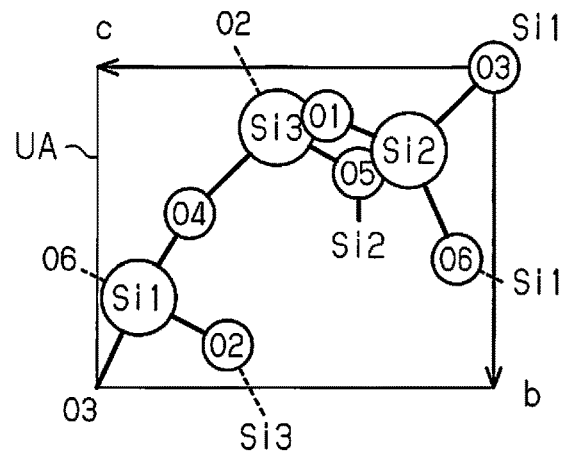
FIG. 2 is an a-axial projection view in one example of the basic divisional unit in the present disclosure.

As indicated by a broken line in the a-axial projection of the low quartz model in FIG. 2, an atom pair composed of Si1 and O6 sandwiches a b-axis in each crystal lattice UA, and an atom pair composed of Si3 and O2 sandwiches a c-axis in each crystal lattice UA. It is recognized that in order that an atom group composed of a plurality of atoms included in the crystal lattice UA is treated individually as the basic divisional unit, an atom pair composed of independent atoms should be set as a division atom pair and each of the above two atom pairs should be set as the division atom pair.

Figure 3:
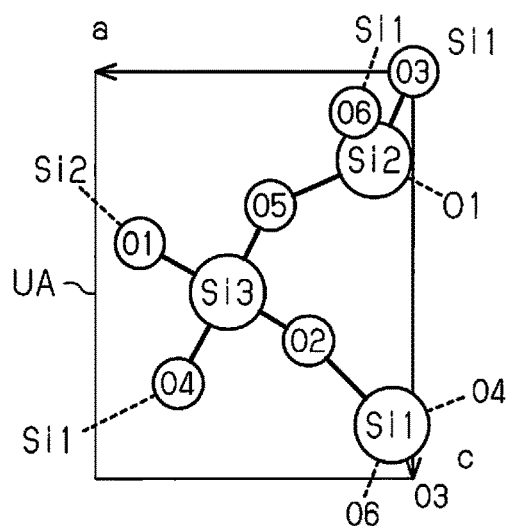
FIG. 3 is a b-axial projection view in one example of the basic divisional unit in the present disclosure.

As indicated by a broken line in a b-axial projection of the low quartz model in FIG. 3, an atom pair composed of Si1 and O6 sandwiches an a-axis in each crystal lattice UA, and an atom pair composed of Si1 and O4 sandwiches a c-axis in each crystal lattice UA. Further, an atom pair composed of Si2 and O1 also sandwiches the c-axis in each crystal lattice UA. It is recognized that each of the above three atom pairs should be set as a division atom pair in order that an atom group composed of a plurality of atoms included in the crystal lattice UA is treated individually as the basic divisional unit, unlike the recognition based on the a-axial projection.

Figure 4:
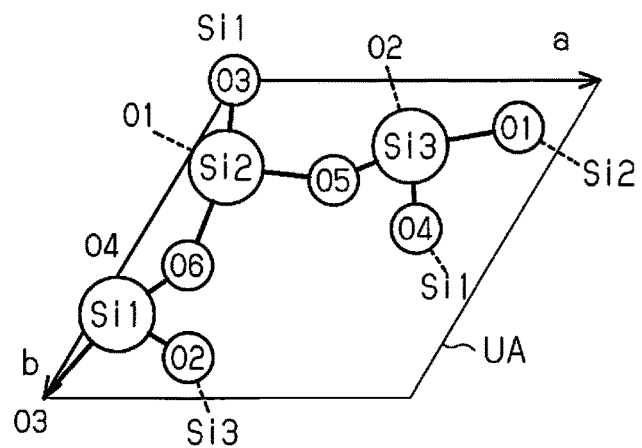
FIG. 4 is a c-axial projection view in one example of the basic divisional unit in the present disclosure.

As indicated by a broken line in the c-axial projection of the low quartz model in FIG. 4, the atom pair composed of Si2 and O1 sandwiches a b-axis in each crystal lattice UA, and the atom pair. composed of Si3 and O2 sandwiches an a-axis in each crystal lattice UA. It is recognized that each of the above two atom pairs should be set as a division atom pair in order that an atom group composed of a plurality of atoms included in the crystal lattice UA is treated individually as the basic divisional unit, unlike the recognition based on the a-axial projection and the b-axial projection.

Information that is obtained from a projection drawing along a single crystal axis is insufficient for a case where each basic divisional unit based on the atom group included in one crystal lattice UA is treated individually in the low quartz model. It is extremely difficult to set such division atom pairs individually for three-dimensional crystal models having a complicated structure composed of thousands of atoms.

Figure 5:
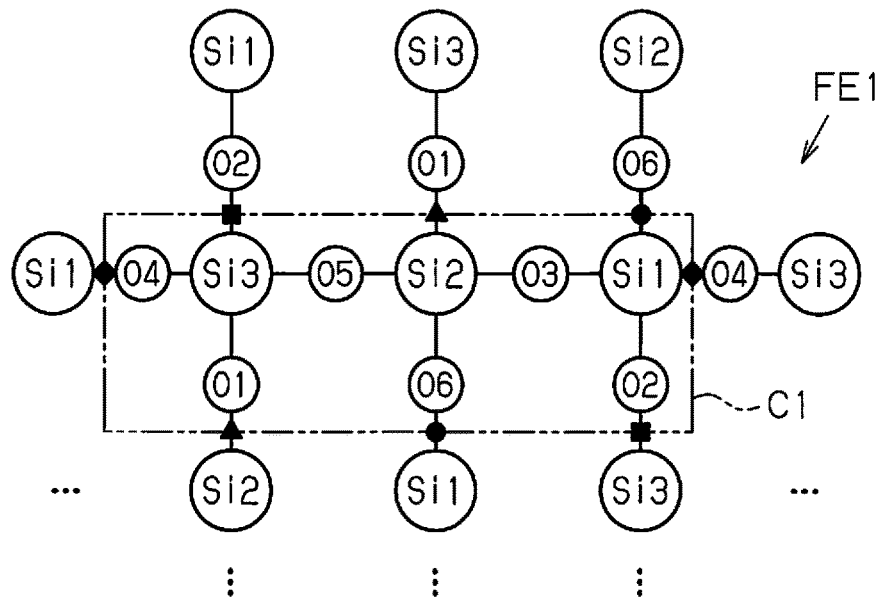
FIG. 5 is a diagram schematically illustrating one example of the basic divisional unit in the present disclosure.

A form of bonding between atoms in the low quartz model can be expressed as a two-dimensional diagram based on the above projection drawing as shown in FIG. 5. In FIG. 5, three Si atoms and six O atoms composing the atom group included in the basic divisional unit C1 are surrounded by an alternate long dashed double-short dashed line.

The fragment model is an atom group composed of atoms bonded to each other in constituent atoms of a crystal model. When each of the basic divisional units C1 is created as the fragment model, constituent atoms of one basic divisional unit C1 and another basic divisional unit C1 are treated in a divided manner. That is, when each of the basic divisional units C1 is created as the fragment model, the following four kinds of atom pairs are defined for each of the basic divisional units C1 as the division atom pair that is an atom pair to be divided in the crystal model.

BDA (Si1)-BAA (O6): filled-in circles in FIG. 5.
BDA (Si2)-BAA (O1): filled-in triangles in FIG. 5.
BDA (Si3)-BAA (O2): filled-in squares in FIG. 5.
BDA (Si1)-BAA (O4): filled-in rhombuses in FIG. 5.

When the right side in FIG. 5 is a terminal in the crystal model, an atom group composed of Si3—O4 is treated as a terminal fragment model FE1. As a result, unlike the above example of O3, namely, an example where one atom across a plurality of crystal lattices UA is present, the basic divisional unit C1 is divided so that an atom that coexists between the adjacent basic divisional units C1 is not present. For this reason, a fragment model corresponding to the basic divisional unit C1 and another terminal fragment model FE1 are created.

Figure 6:
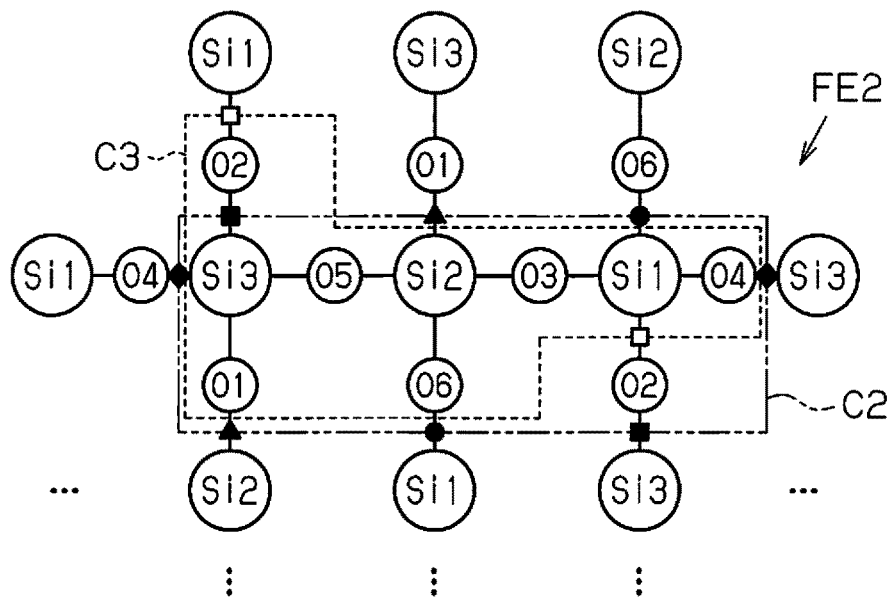
FIG. 6 is a diagram schematically illustrating another example of the basic divisional unit in the present disclosure.

As shown in FIG. 6, a fragment model whose size is the same as the basic divisional unit C1 in FIG. 5 is determined also by a division atom pair different from the above division atom pair. For example, similarly to the basic divisional unit C1, three Si atoms and six O atoms composing an atom group included in a crystal lattice are determined as one basic divisional unit C2 also on a position that is shifted rightward from the basic divisional unit C1 by the amount corresponding to one oxygen atom as viewed in the drawing. The following four kinds of atom pairs are determined as the division atom pair for each basic divisional unit C2, and thus the basic divisional unit C2 is created as the fragment model. The size of the basic divisional unit C2 is the same as that of the basic divisional unit C1, and the position of the basic divisional unit C2 in the crystal model is different from that of the basic divisional unit C1.

BDA (Si1)-BAA (O6): filled-in circles in FIG. 6.
BDA (Si2)-BAA (O1): filled-in triangles in FIG. 6.
BDA (Si3)-BAA (O2): filled-in squares in FIG. 6.
BDA (Si3)-BAA (O4): filled-in rhombuses in FIG. 6.

When the right side in FIG. 6 is a terminal in the crystal model, an atom group composed of Si3 is treated as a terminal fragment model FE2.

In such a manner, since the basic divisional unit includes three Si atoms and six O atoms and these atoms may exist as an atom group where they are bonded to each other, different basic divisional units can be set on the position shifted by the amount corresponding to one oxygen atom. That is, different division forms are used for such setting of basic divisional units. Even if the basic divisional units with the same size are used, structures and formal charges of the terminal fragment models vary when the division atom pairs that are determined for the respective basic divisional units are different from each other. As a result, calculated results of an FMO method, such as electronic states of the crystal model and interaction energies between the crystal model and another molecular model are different from each other.

Four groups of BDA-BAA, namely, division atom pairs are set in the basic divisional unit including three Si atoms and six O atoms, and only one of the four groups of BDA-BAA is different between the basic divisional unit C1 and the basic divisional unit C2. Basic divisional units with the same sizes are created by setting the basic divisional unit for each of the four groups of BDA-BAA in a shifting manner as described above. For example, also when Si3—O2 is changed into Si1—O2 in the four groups of BDA-BAA in the basic divisional unit C2, the basic divisional unit C3 composed of three Si atoms and six O atoms is created as surrounded by a broken line in FIG. 6. In this way, $2^4$ (fourth power of two, namely, sixteen) forms that are different from each other are present for the basic divisional units with the same size obtained by setting 4 groups of BDA-BAA.

Further, the crystal model includes excessive atom groups besides a plurality of basic divisional units like the above terminal fragment models FE1 and FE2. For this reason, although the basic divisional unit in the present embodiment is the minimum repetition unit that determines repetition of the division atom pair, it is not a unit that determines the fragment model. As described above, the fragment model is an atom group composed of bonded atoms in the constituent atoms of a crystal model. A plurality of fragment models is created from one basic divisional unit in some cases or one fragment model is created across a plurality of basic divisional units in other cases according to the division atom pairs that are determined in the respective basic divisional unit. In any of the cases, when the division atom pairs that are determined for the respective basic divisional units are different from each other, the structures and the formal charges of the terminal fragment models are different from each other.

A fragment model creating system for creating a fragment model from a crystal model will now be described below.

Figure 7:
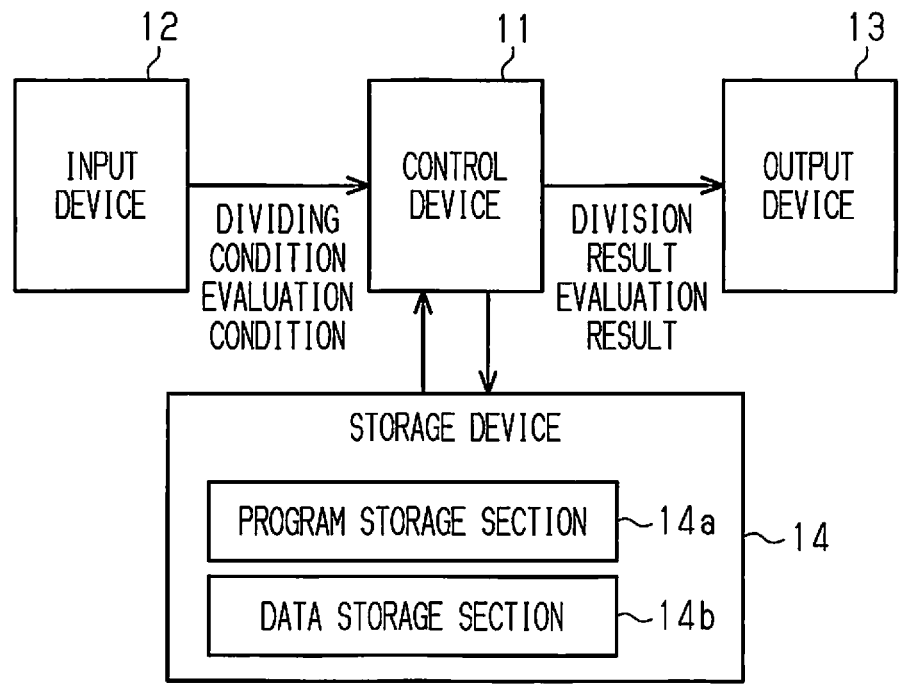
FIG. 7 is a block diagram functionally illustrating a fragment model creating device according to a first embodiment of the present disclosure.

The fragment model creating system includes a control device 11 as the fragment creating device as shown in FIG. 7. The control device 11 is connected to an input device 12, an output device 13, and a storage device 14. The fragment model creating system may be a distributed computer systems in which at least one of the input device 12, the output device 13, and the storage device 14 is connected to the control device 11 via a network, or all the control device 11, the input device 12, the output device 13, and the storage device 14 may be contained in one computer system.

The control device 11 creates a fragment model according to a procedure expressed in a fragment model creating program stored in the storage device 14 by using data input from the input device 12 and data stored in the storage device 14, and outputs a created result of the fragment model from the output device 13.

The input device 12 inputs data necessary for creating a fragment model into the control device 11. The data includes, for example, crystal model data Dcry, basic divisional unit data Dcel, division atom pair candidate Pdev, and basis function data Dbasis as division conditions. This data further includes a number of output forms Nout as an evaluation condition.

The storage device 14 includes a program storage section 14a and a data storage section 14b. The program storage section 14a stores the fragment model creating program for creating a fragment model. The data storage section 14b stores data input from the input device 12, various data used at a time of executing the fragment model creating program, such as the number of basis functions necessary for each type of atoms, the number of electrons in each type of atoms, and the atomic radius of each type of atoms.

The output device 13 outputs data about types of atoms included in each of a plurality of fragment models created by the control device 11, the coordinates of atoms included in each of the fragment models, and the charge state of each of the fragment models as division results. Further, the output device 13 outputs the division result according to each division form of the crystal model. Further, the output device 13 outputs, as evaluation results, data in which the division results created by the control device 11 are associated with evaluated values of the division results.

The data stored in the storage device 14 will be described below with reference to FIG. 8.

Figure 8:
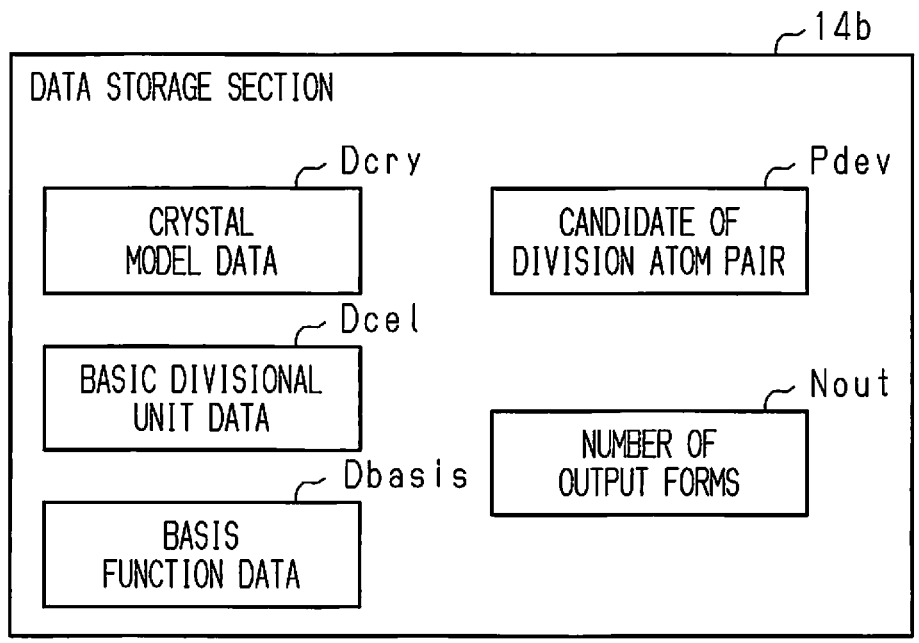
FIG. 8 is a diagram illustrating a type of data to be stored in a storage device according to the first embodiment.

The crystal model data Dcry, the basic divisional unit data Dcel, the division atom pair candidates Pdev, the basis function data Dbasis, and the number of output forms Nout are stored in the data storage section 14b as shown in FIG. 8. These pieces of data are input from the input device 12.

The crystal model data Dcry represents all the atoms composing the crystal model as specific atoms, the atom types, and the atom coordinates of the constituent atoms. Any one of the atoms included in one basic divisional unit is associated with the data about each specific atom such as the atom type and the atom coordinate in the crystal model data Dcry. A data format of the crystal model data Dcry may be such that, for example, the constituent atoms are read in the ascending order or in the descending order of the distance from an origin of the atom coordinate.

Such types of the atoms in the crystal model data Dcry are created by repeating a symmetry operation such as translation and rotation according to a space group of the low quartz on, for example, each of the constituent atoms in the crystal lattice UA that is the unit lattice of the low quartz at a desired number of times. Further, the coordinates of the atoms in the crystal model data Dcry are created by repeating the symmetry operation such as translation and rotation according to the space group of the low quartz on, for example, each of the constituent atoms in the crystal lattice UA at a desired number of times. Since the execution of only the repetition of the translation operation of the crystal lattice UA at a limited number of times destroys the periodic bonding of the atoms composing the crystal model in a terminal portion of the crystal model, in order to compensate this, a plurality of Si atoms and O atoms are added to the terminal portion. Further, when, for example, data about replacement of atoms including types of replaced atoms and data about deletion of atoms are associated with data corresponding to some constituent atoms in the data created in such a manner, the crystal model data Dcry where some constituent atoms are replaced or the crystal model data Dcry having a point defect are created. Further, when the types and the coordinates of the atoms to be added are added, the crystal model data Dcry to which atoms are partially added or the crystal model data Dcry that includes a step or kink is created. Further, when the translation operation is performed on the coordinates of some atom groups, the crystal model data Dcry having a line defect or a plane defect is created.

In the basic divisional unit data Dcel, each of a plurality of atoms included in one basic divisional unit is shown as a specific atom, and the atom types of the respective constituent atoms are shown. The basic divisional unit is a three-dimensional unit atom group that is repeated in the crystal model, and is the minimum space unit that determines the division atom pair candidate Pdev. When the crystal model data Dcry is created by the user, the basic divisional unit is preset within a range of the crystal model by the user. The basic divisional unit is set as, for example, the atom group included in the single crystal lattice UA or the atom group included in the crystal lattices UA.

The division atom pair candidate Pdev is a candidate of a division atom pair determined for each basic divisional unit. That is, the division atom pair candidate Pdev is a combination of n atoms (n is an integer that is 1 or greater) set as candidates of BDA and n atoms set as candidates of BAA in the constituent atoms of the basic divisional unit. The division atom pair candidate Pdev may include one kind of atom pair or two or more kinds of atom pairs. For example, when the atoms included in the basic divisional unit are Si1 to Si3 and O1 to O6, the division atom pair candidate Pdev may include Si1—O6, Si2—O1, Si3—O2, and Si1—O4, or Si1—O6, Si2—O1, Si3—O2, and Si3—O4 as candidates of BDA-BAA as a combination of BDA and BAA. The control device 11 creates a fragment model for each combination of a BDA candidate and a BAA candidate, namely, each division form of the crystal model.

The basis function data Dbasis represents the basis function that is used for calculation of a charge state in the created fragment model.

The number of output forms Nout represents the number of the division results to be output for the division forms of the crystal model. When the number of the division forms determined by the division atom pair candidate Pdev is sixteen and the number of output forms Nout is three, three kinds of the division results are output in the descending order of the evaluated values in sixteen types of the division results. A priority of the fragment models is determined by the control device 11 based on a polarization of the formal charge of each fragment model in the crystal model.

Figure 11:
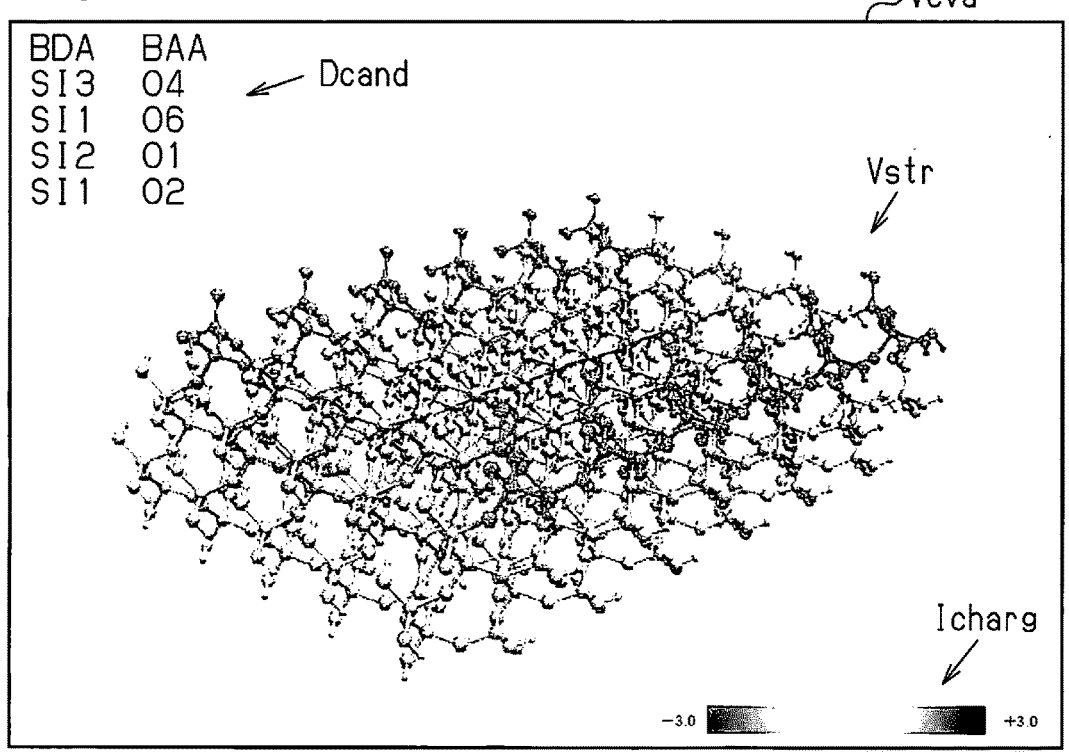
FIG. 11 is a diagram in which the charge state in a crystal model is indicated with a corresponding color in one example of the display view of the evaluation result according to the first embodiment.
Figure 12:
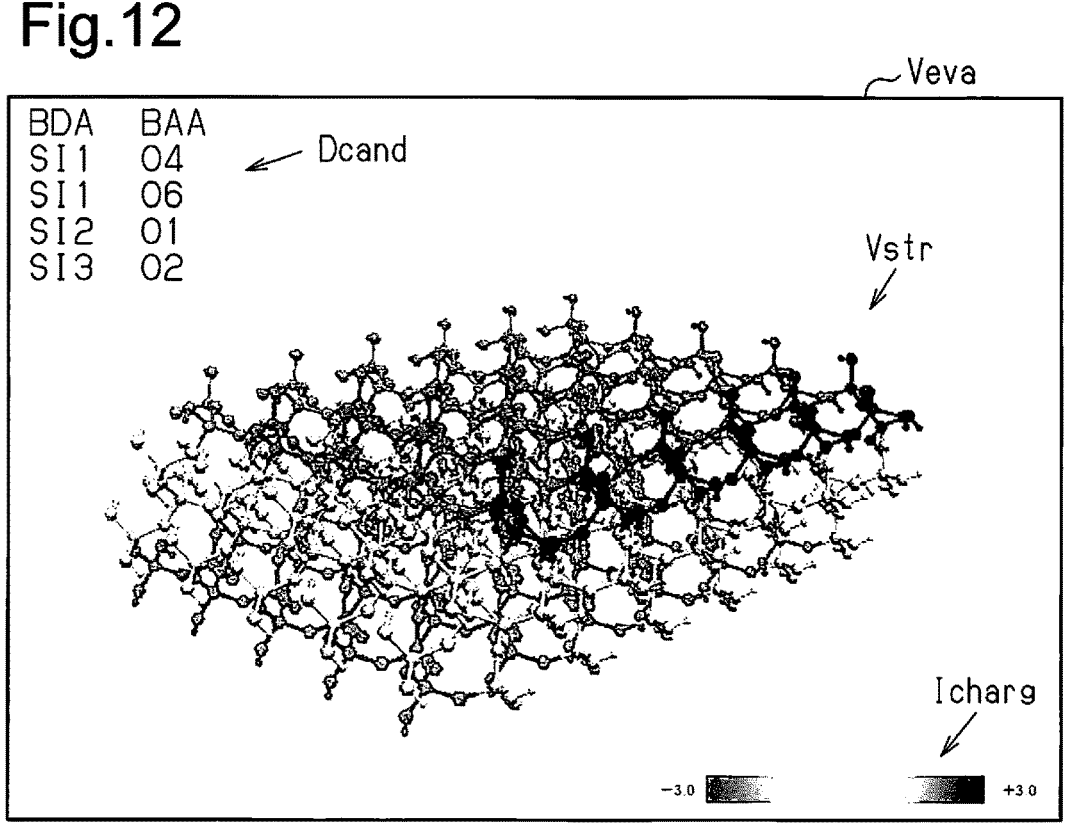
FIG. 12 is a diagram in which the charge state in a crystal model is indicated with a corresponding color in one example of the display view of the evaluation result according to the first embodiment.
Figure 13:
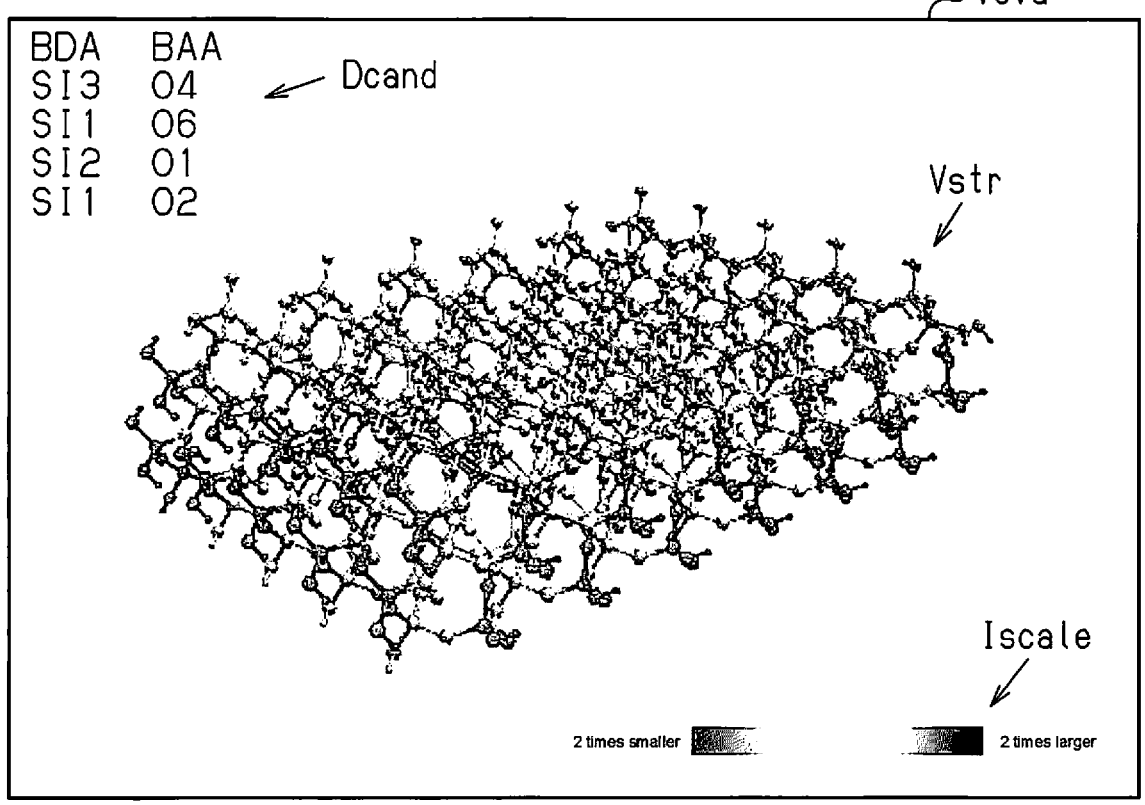
FIG. 13 is a diagram in which the size of the fragment model in the crystal model is indicated with a corresponding color in one example of the display view of the evaluation result according to the first embodiment.

FIGS. 9 and 10 illustrate one example of a display view that displays a charge state list included in the division results, and one example of a display view that displays evaluation results. FIGS. 11 to 13 illustrate an example where the charge state in the crystal model is indicated with a corresponding color, and an example where the size of the fragment model in the crystal model is indicated with a corresponding color as one example of the display view of the evaluation results. That is, differences in the charge state and the size of the fragment model are indicated with different colors. "Color" includes also white and black, and "difference in color" includes any differences related to color elements (attributes) such as hue, brightness, and chroma.

The division results include a coordinate list representing the coordinates of the constituent atoms included in the fragment model, and a charge state list representing the charge state of the fragment models for each division form of the crystal model.

In the coordinate list, the types of atoms included in the fragment model are associated with the coordinates and are shown according to each fragment model.

In the charge state list, each of all the fragment models created for each division form of the crystal model is shown in a form of the list according to each charge state of the fragment model. For example, in the fragment model including Si1 to Si3, which are three Si atoms, and O1 to O6, which are six O atoms, the charge state of the fragment model where BDA is Si1 is treated to be different from the charge state of fragment model where BDA is Si2.

As shown in FIG. 9, on a display view Vfrag of the charge state list, for example, a type number N to be allocated to each charge state of the fragment model is associated with seven entries shown below. For example, when a constitutional formula of the fragment model is displayed, a colon (:) is added to the atoms as BDA, and a dash (-) is added to the atoms as BAA so that the atoms as BDA and the atoms as BAA can be grasped by the user.

The chemical formula Cfm of the fragment model
The number Na of atoms included in the fragment model
The number Nb of the basis functions necessary for the fragment model
The atom corresponding to BDA
The atom corresponding to BAA
The number nBDA of BDAs included in the fragment model
The number nBAA of BAAs included in the fragment model
The formal charge Nc of the fragment model
The number Cnt of the fragment models included in the crystal model
The constitutional formula Fname of the fragment model The evaluation results are the evaluated values of the division results, namely, the evaluated values for the candidates of the division atom pair as a combination of a BDA candidate and a BAA candidate. The number of the division results shown in the evaluation results is determined by the number of output forms Nout.

As shown in FIG. 10, a display view Veva, which displays the evaluation results, shows, for example, candidates Dcand of the division atom pair as the combination of a BDA candidate and a BAA candidate individually. Further, division results Dresl of the candidates Dcand of the division atom pair are associated with the candidates Dcand of the division atom pair so as to be displayed. For example, the total sum of absolute values of the formal charge of the crystal model is set as an evaluated value Pseq of each of the division results Dresl, and the division results Dresl are arranged to be displayed in the ascending order of the total sum of the absolute values of the formal charge.

As shown in FIG. 11, the candidate Dcand of the division atom pair and a molecular structure Vstr of the crystal model in one of the division results Dresl are displayed together on the display view Veva, which displays the evaluation results. For example, Si3—O4, Si1—O6, Si2—O1, and Si1—O2 are used as the candidates Dcand of the division atom pair in FIG. 11. The formal charges of the fragment models created based on the candidates Dcand of the division atom pair are indicated with corresponding colors.

When the formal charges of the fragment models are indicated, different colors are associated with different formal charges. The respective colors have different attributes such as hue, brightness, and chroma. The correspondence relationship is displayed as an index Icharg. In FIG. 11, white is associated with the formal charge of neutrality, namely, ±0 as a basis, and black is associated with the formal charges of, for example, +3.0 and −3.0. As the formal charge approaches ±0 from +3.0, and the formal charge approaches ±0 from −3.0, the chroma of the color associated with the formal charge gets close to white from black. That is, the chroma of the color associated with each of the formal charges changes according to the absolute value of each of the formal charges. The upper limit value and the lower limit value of the formal charge at the index Icharg can be suitably changed. As the formal charge changes from the formal charge of ±0 as the standard to the +direction, namely, the positive direction or the −direction, namely, the negative direction, the chroma of the color associated with the formal charge preferably changes so that the color gets closer to black from white. A color corresponding to the formal charge of the fragment model is added to each of the fragment models composing the molecular structure Vstr.

In FIG. 12, similarly to FIG. 11, the candidates Dcand of another division atom pair and the molecular structure Vstr of the crystal model are displayed together. For example, in FIG. 12, Si1—O4, Si1—O6, Si2—O1, and Si3—O2 are used as the candidates Dcand of the division atom pair. The formal charges of the fragment models created based on the candidates Dcand of the division atom pair are indicated with corresponding colors.

As shown in FIG. 13, the element of the evaluation result that is displayed together with the molecular structure Vstr of the crystal model may be the size of each fragment model, and in this case, the size of each fragment model may be indicated with each corresponding color. Also at this time, the candidates Dcand of the division atom pair and the molecular structure Vstr of the crystal model in one of the division results Dresl are displayed together on the display view Veva, which displays the evaluation results.

For example, in FIG. 13, Si3—O4, Si1—O6, Si2—O1, and Si1—O2 are used as the candidates Dcand of division atom pair. The size of each fragment model created based on the candidates Dcand of the division atom pair is indicated with each corresponding color. When the sizes of the fragment models are displayed, different colors are associated with different sizes of the fragment models. The respective colors have different attributes such as hue, brightness, and chroma. The correspondence relationships are displayed as indexes Iscale. In FIG. 13, the atom group included in the basic divisional unit data Dcel is set as a standard size. White is associated with the standard size, and for example, black is associated with sizes that is two times and one-half larger than the standard size. As the size of the atom group gets closer from the size that is two times to the standard size or from the size that is ½ to the standard size, the chroma of the color associated with the size of the atom group changes so that the color gets closer to white from black. The upper limit value and the lower limit value of the size at the index Iscale can be suitably changed. As the size of the atom group changes towards a direction where it becomes larger from the standard size or in a direction where it becomes smaller, the chroma of the color associated with the size of the atom group preferably changes so that the color gradually changes from white into black.

The molecular structure Vstr shown in FIGS. 11 to 13 preferably rotates about the central coordinate of the molecular structure Vstr on the display view Veva according to an operation of a human interface device such as a mouse or a touch pad. In this case, one molecular structure Vstr can be displayed from any one of different viewpoints on the display view Veva. Although colors that are associated with the formal charge and the size are provided to each fragment model as described above, some fragment models are displayed behind the other fragment models, namely, the display of some fragment models is hidden by the display of the other fragment models. As to this point, one molecular structure Vstr is displayed from different viewpoints, so that the color of the hidden fragment model is visually recognizable. For this reason, the user can easily understand distributions of the formal charge and the size in the molecular structure Vstr.

The control device 11 will now be described with reference to FIG. 14.

Figure 14:
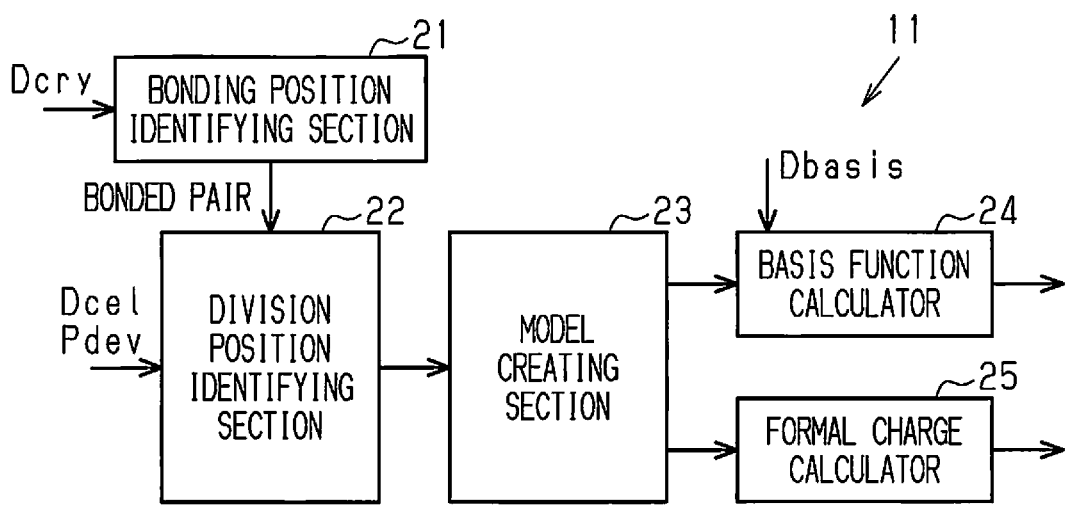
FIG. 14 is a block diagram functionally illustrating a control device according to the first embodiment.

As shown in FIG. 14, the control device 11 includes a bonding position identifying section 21, a division position identifying section 22, a model creating section 23, a formal charge calculator 25, and a basis function calculator 24.

The bonding position identifying section 21 calculates an interatomic distance that is the distance between two different atoms in the atom pair for all the constituent atoms in the crystal model by using the crystal model data Dcry. Further, the bonding position identifying section 21 extracts a bonded pair that is an atom pair in which both atoms are bonded from the atom pair whose interatomic distance is calculated, and outputs the extracted result to the division position identifying section 22. For example, the bonding position identifying section 21 refers to the extracted bonded pair and associates the constituent atoms included in the crystal model data Dcry with the other atom to which each of the constituent atoms is bonded so as to generate data representing the bonded pair. At this time, the bonding position identifying section 21 calculates, for example, the sum of the atomic radii of the two atoms in one atomic pair as an ideal distance between the atoms. When the calculated interatomic distance is within a predetermined threshold of a setting region with respect to the ideal distance, the bonding position identifying section 21 outputs the two atoms as the bonded pair. The setting region with respect to the ideal distance is different, for example, according to types of atoms in the atom pair and the structures of the crystal model.

The division position identifying section 22 extracts the combination of BDA and BAA in the constituent atoms of the crystal model data Dcry by using the crystal model data Dcry, the basic divisional unit data Dcel, and the division atom pair candidate Pdev.

At this time, the division position identifying section 22 refers to the crystal model data Dcry and the basic divisional unit data Dcel, and associates the constituent atoms of the crystal model with any of the constituent atoms in the basic divisional unit. Atoms corresponding to candidates of division atom pairs for each of the basic divisional units are extracted as candidates of BDA and BAA. The division position identifying section 22 identifies a combination included in the extracted bonded pair as the combination of BDA and BAA by using the bonded pair that is the output result from the bonding position identifying section 21. On the other hand, the division position identifying section 22 identifies a combination that is not included in the extracted bonded pair simply as a non-boning atom pair in which the atoms are not bonded.

For example, by using data representing the bonded pair created by the bonding position identifying section 21 the division position identifying section 22 determines whether to associate each of the constituent atoms included in the crystal model data Dcry with BDA or BAA. Further, as to each of the constituent atoms included in the crystal model data Dcry, when the constituent atoms are included in a non-bonded atom pair, the division position identifying section 22 deletes the atoms to be bonded associated with the constituent atoms from the data. As a result, the division position identifying section 22 generates data that associates, with each of the constituent atoms included in the crystal model data Dcry, the following factors: (i) an atom to be bonded in the constituent atoms, (ii) whether the constituent atom is BDA or not, and (iii) whether the constituent atom is BAA or not. At this time, when the crystal model data Dcry is data including a replaced atom, one of BDA and BAA does not have to be associated with the replaced atoms. The association of BDA and BAA with replaced atoms is suitably set by the division position identifying section 22 according to a request of an analysis on the replaced atoms. For example, when the replaced atoms and the constituent atoms of the basic divisional unit are requested to be treated similarly, any one of BDA and BAA may be associated with the replaced atoms similarly to the constituent atoms of the basic divisional unit. On the other hand, when the replaced atoms and the other atoms are requested to be treated as a bonded atom pair, any one of BDA and BAA does not have to be associated with the replaced atoms. Further, when the crystal model data Dcry includes deleted atoms and the crystal model data Dcry includes added atoms, the division position identifying section 22 suitably sets the association of BDA or BAA with the atoms similarly to the replaced atoms.

The model creating section 23 creates a plurality of fragment models from the crystal model by using the identified result in the bonding position identifying section 21, the identified result in the division position identifying section 22, and the crystal model data Dcry. At this time, the model creating section 23 excludes BDA, BAA, and a non-bonded atom pair identified by the division position identifying section 22 from the bonded pair identified by the bonding position identifying section 21 so as to correct the bonded pair, and treats this corrected bonded pair. The model creating section 23 identifies each of atom groups in which the corrected bonded pairs are connected in the constituent atoms of the crystal model, and creates each fragment model associated with each of the identified atom groups. Further, the model creating section 23 functions as an output section and generates model data in which each of the constituent atoms of the crystal model is associated with the fragment model including each of the constituent atoms, and outputs the model data to the basis function calculator 24 and the formal charge calculator 25.

The basis function calculator 24 calculates the number of the basis functions necessary for the fragment models by using the model data as the output result of the model creating section 23 and the basis function data Dbasis, and outputs the calculated result to the output device 13. Further, the formal charge calculator 25 calculates the formal charge of each fragment model by using the model data as the output result of the model creating section 23 and the number of electrons of each atom, and outputs the calculated results to the output device 13.

Examples of processes in the bonding position identifying section 21 and the division position identifying section 22 will be described with reference to FIG. 15. FIGS. 15A, 15B, and 15C are diagrams where data created by the bonding position identifying section 21 and the division position identifying section 22 are schematically visualized by an atom coordinate system.

Figure 15A:
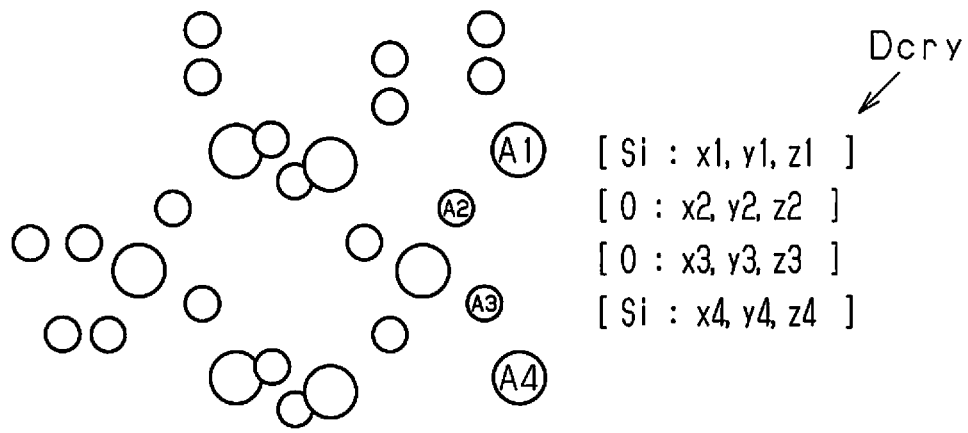
FIGS. 15A, 15B, and 15C are diagrams schematically illustrating a process executed by the control device according to the first embodiment.

As shown in FIG. 15A, in the crystal model data Dcry treated by the bonding position identifying section 21, types of the constituent atoms A1 to A4 of the crystal model are associated with coordinates in the atom coordinate system. For example, as to the atom A1, the type of this atom is Si, and its coordinate is (x1, y1, z1). As to the atom A2, the type of this atom is O, and its coordinate is (x2, y2, z2). As to the atom A3, the type of this atom is O, and its coordinate is (x3, y3, z3). As to the atom A4, the type of this atom is Si, and its coordinate is (x4, y4, z4).

Figure 15B:
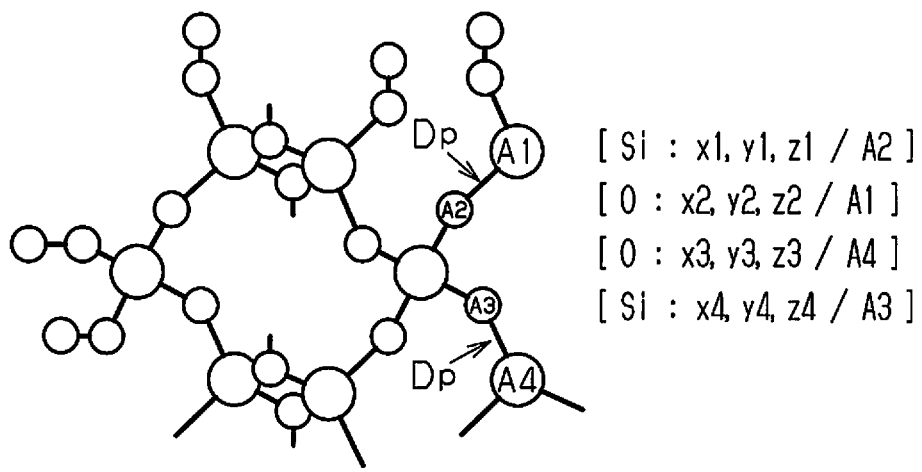

As shown in FIG. 15B, the bonding position identifying section 21 further adds bonded pair data Dp to the crystal model data Dcry. The bonded pair data Dp represents whether bonding is formed between two atoms in each atom pair, namely, whether the atom pair is a bonded pair. For example, the atom A1 in the constituent atoms A1 to A4 included in the crystal model data Dcry is associated with the atom A2, to which the atom A1 is bonded, and the atom A2 is associated with the atom A1, to which the atom A2 is bonded. Further, the atom A3 is associated with the atom A4, to which the atom A3 is bonded, and the atom A4 is associated with the atom A3, to which the atom A4 is bonded.

Figure 15C:
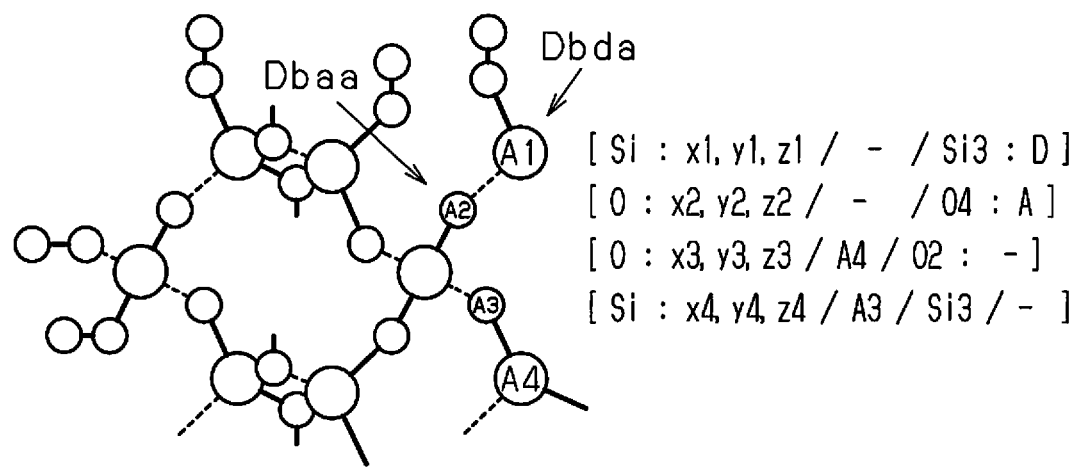

As shown in FIG. 15C, the division position identifying section 22 identifies which constituent atom of the basic divisional unit is each of the constituent atoms of the crystal model. For example, the atom A1 is associated with Si3, and the atom A2 is associated with O4. Further, the atom A3 is associated with O2, and the atom A4 is associated with Si3.

Further, the division position identifying section 22 further adds division atom pair data Dbda and Dbaa to the data created by the bonding position identifying section 21. The division atom pair data Dbda represents whether each of the constituent atoms of the crystal model is BDA. The division atom pair data Dbaa represents whether each of the constituent atoms of the crystal model is BAA. For example, the atom A1 is associated with D representing BDA, and the atom A2 is associated with A representing BAA. The association of the constituent atoms A1 and A2 with their bonding destinations is deleted according to the association of BDA or BAA. On the other hand, since the constituent atoms A3 and A4 are not associated with BDA or BAA, the association of them with their bonding destination is maintained.

A fragment model creating method that is executed by the fragment model creating system will be described with reference to FIG. 16.

Figure 16:
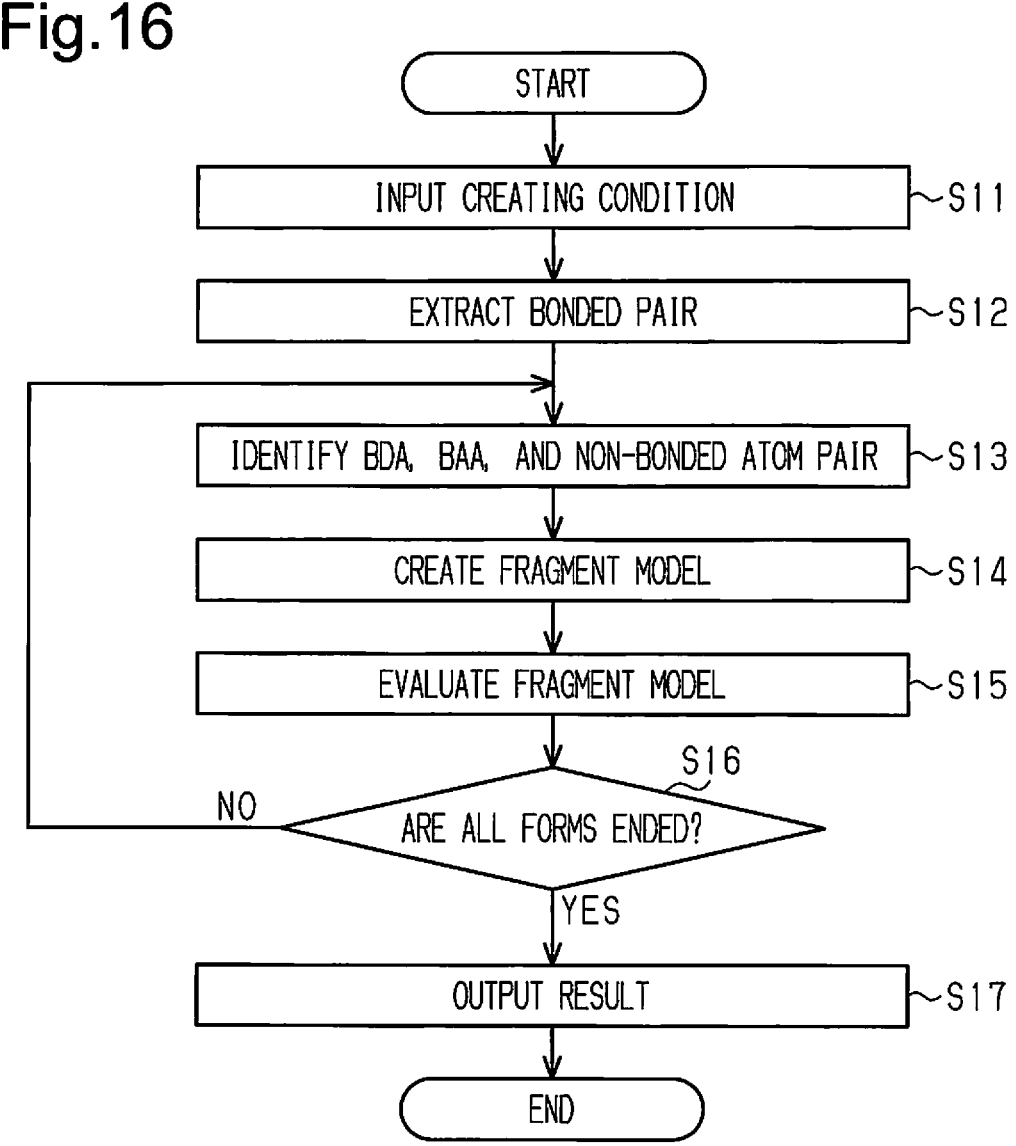
FIG. 16 is a flowchart illustrating a procedure for creating the fragment model according to the first embodiment.

When the procedure is started, first, a creating condition of the fragment model is input into the input device 12 (step S11) as shown in FIG. 16. At this time, the crystal model data Dcry, the basic divisional unit data Dcel, the division atom pair candidate Pdev, the basis function data Dbasis, and the number of output forms Nout are input as one input file following a preset format into the input device 12. For example, when low quartz shown in FIG. 1 is used as the crystal model, all coordinates of Si included in the crystal model and all coordinates of O are input as the crystal model data Dcry. The control device 11 stores the input file input into the input device 12 in a storage device 14.

The control device 11 calculates an interatomic distance that is the distance between the atoms in an atom pair composed of different two atoms for all the constituent atoms in the crystal model by using the crystal model data Dcry. The control device 11 then extracts a bonded pair that is the atom pair in which the atoms are bonded from the atom pairs whose interatomic distances have been calculated so as to output the extracted result (step S12).

The control device 11 identifies BDA, BAA, and non-bonded atom pair in the constituent atoms of the crystal model data Dcry by using the crystal model data Dcry, the basic divisional unit data Dcel, and the division atom pair candidate Pdev (step S13).

For example, Si3O6 is preset as the basic divisional unit for the crystal model shown in FIG. 1, and Si1—O6, Si2—O1, Si3—O2, and Si1—O4 are set as candidates of the division atom pair.

The atoms corresponding to Si1, Si2, and Si3 are extracted as the candidates of BDA, and the atoms corresponding to O1, O2, O4, and O6 are extracted as candidates of BAA for each of the basic divisional units. A combination included in the extracted bonded pair is identified as the combination of BDA and BAA. On the other hand, a combination that is not included in the extracted bonded pair is simply identified as a non-bonded atom pair where bonding is not carried out.

The control device 11 then creates a plurality of fragment models from the crystal model by using data about association of the bonded pair, BDA, BAA, and the non-bonded atom pair, and the crystal model data Dcry. That is, the control device 11 divides the crystal model into a plurality of fragment models.

At this time, the control device 11 (the model creating section 23) treats each of atom groups composed of bonded atoms in the constituent atoms of the crystal model as the fragment model with reference to the bonded pair, BDA, BAA, and non-bonded atom pair (step S14). The control device 11 calculates the total sum of absolute values of the formal charges in the created fragment models and the number of the basis functions necessary for the respective fragment models (step S15). The control device 11 determines whether the fragment model has been created for all division forms determined by the division atom pair candidates Pdev (step S16).

When the fragment model has not been created for all the division forms ("NO" at step S16), the control device 11 repeats step S13 to step S16 by using another division atom pair whose fragment model has not been created.

When the fragment model has been created for all the division forms ("YES" at step S16), the control device 11 assigns priorities to all the division forms in the ascending order of the total sum of the absolute values of the formal charges in the fragment model. At this time, priorities are assigned to the division forms having the same total sums of the absolute values of the formal charges in the ascending order of the maximum value of the size of the fragment model included in each division form, that is, the maximum value of the number of the basis functions necessary for the fragment model. The control device 11 outputs the division result and the evaluation result from the output device 13 with reference to the assigned priorities (step S17).

The first embodiment achieves the following advantages.

(1) The crystal model to be used for creating the fragment model is treated as an aggregate of the basic divisional units C1 and C2. The candidates of the division atom pair are set for each of the basic divisional units C1 and C2 so as to be identified as division atom pairs. For this reason, setting accuracy of BDA and BAA is improved, and BDA and BAA can be easily set.

(2) The division position identifying section 22 identifies BDA and BAA, and outputs the identified BDA and BAA for each constitutional formula of the fragment model. For this reason, the user can understand such a division atom pair for each fragment model.

(3) Information about division atom pair included in the fragment model is required for a merging process that treats two different fragment models as one fragment model. Further, this information is effectively utilized for improving accuracy of the calculation of the electron state of the crystal model by using the fragment model. The configuration according to (2) enables such useful information to be output.

(4) The division position identifying section 22 sets a plurality of different candidates as the division form of the crystal model, and identifies the division atom pair for each division form. The model creating section 23 creates the fragment model for each division form by using the division atom pair of each division form. For this reason, diversity of the fragment model to be created can be heightened.

(5) As described in (3), when the electron states of the crystal models are calculated by using the fragment models, the calculated results frequently vary according to the sizes of the fragment models or the types of the constituent atoms in the fragment models. The diversity of the sizes of the fragment models and the types of the constituent atoms in the fragment models is useful for understanding of a tendency of the calculation accuracy of the electron state of the crystal model. The configuration according to (4) enables such useful information to be output.

(6) The evaluation results output from the output device 13 indicate the evaluated values of a plurality of division results, namely, the evaluated values of the candidates of the division atom pair as the combination of a BDA candidate and a BAA candidate. For this reason, the user can easily understand that which of the fragment models created for the respective candidates is suitable for the calculation of the electron state in the crystal model. Particularly, the formal charges and the sizes of the fragment models are displayed by giving colors having attributes of different colors with different hue, brightness and chroma, so that the user understands distributions of the formal charges and the sizes in the crystal model three-dimensionally, and as a result, visibility of the formal charge and the size in each fragment model is improved.

Second Embodiment

A second embodiment will now be described with reference to FIGS. 17 to 22. The second embodiment is different from the first embodiment in that the merging process for again setting some of the created fragment models and the other fragment models as one atom group and creating that atom group as new one fragment model is executed. Therefore, the second embodiment mainly describes points different from the first embodiment, and the same reference symbols as those in the first embodiment are given to the components having the overlapped functions in the first embodiment, and description thereof is omitted.

In calculations of the electron state of a crystal model using fragment models, calculations of the electron state in respective fragment models can be performed in parallel. In such a calculating system, a variation in the size of each fragment subject to parallel computation, namely, a variation in parallel granularity is reduced so that efficiency of the calculation is increased. Further, the number of fragments whose sizes are extremely small in a plurality of fragments is reduced so that the efficiency of the calculation is increased. Further, the above merging process reduces a variation in the size of each fragment further than a case where the merging process is not executed, and reduces the number of fragments whose sizes are extremely small so that accuracy of the calculation is improved.

Figure 17:
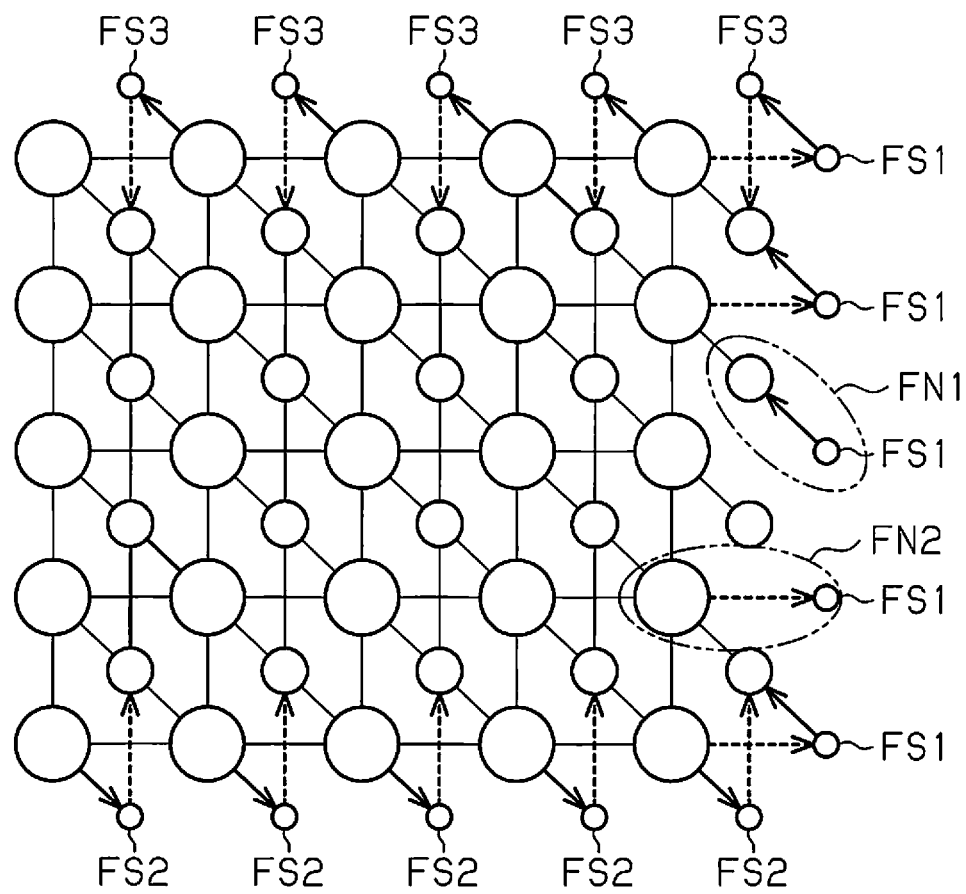
FIG. 17 is a diagram schematically illustrating one example of a subject to be merged according to a second embodiment.

The fragment model that is subject to the merging process will now be described with reference to FIG. 17. In FIG. 17, each fragment model is indicated by a circle. The diameter of each circle indicates the size of a corresponding fragment model. The bonding of BDA and BAA between the different fragment models is indicated by a thin line. The fragment model indicated by the largest circle is a fragment model in a bulk in the crystal model, and the fragment model indicated by the smallest circle is a fragment model at a terminal created around the crystal model. The fragment model indicated by a middle size circle is a fragment model at a terminal created at an end surface on the side closer to the viewer of the sheet of the drawing in the crystal model.

Terminal fragment models FS1, FS2 and FS3, which are fragment models at terminal, are created at the terminal of the crystal model as shown in FIG. 17. The constituent atoms and the sizes of the terminal fragment models FS1, FS2 and FS3 are different from each other according to creating conditions of the fragment models such as constituent atoms of a basic divisional unit and candidates of the division atom pair. The terminal fragment models FS1, FS2 and FS3 are portions that remain at the terminal when the fragment models are created. The sizes of the terminal fragment models FS1, FS2 and FS3 are smaller than the sizes of the other fragment models, namely, a non-terminal fragment models. Such terminal fragment models FS1, FS2 and FS3 include the division atom pair similarly to the non-terminal fragment model, but division atom pairs included in the terminal fragment models FS1, FS2 and FS3 are different from a division atom pair of the non-terminal fragment model.

For example, it is assumed that the fragment model that is arranged on the left of each terminal fragment model FS1 in FIG. 17 is $Si_3O_6$, and its charge state is Si1: Si2: Si3: O1—O2—O3O4—O5O6—. It is also assumed that each terminal fragment model FS1 is $SiO_3H_2$, and its charge state is Si1: O3O4—O6H3H6. In such a case, both the terminal and non-terminal fragment models include the division atom pair, but each non-terminal fragment model arranged on the left of the terminal fragment model FS1 includes Si1, Si2, and Si3 as BDA, and includes O1, O2, O4, and O6 as BAA, whereas the terminal fragment model FS1 includes Si1 as BDA and O4 as BAA.

As described above, candidates of division atom pairs included in the terminal fragment models FS1, FS2 and FS3 are different from candidates of the division atom pairs included in the non-terminal fragment models. The bonding form of the terminal fragment models FS1, FS2 and FS3 and the non-terminal fragment models adjacent to them varies according to the division atom pairs included in the terminal fragment models FS1, FS2 and FS3.

For example, it is assumed that each terminal fragment model FS1 is SiO3H2, and its charge state is Si1: O3O4—O6H3H6. In such a case, in one bonding form of the terminal fragment model FS1, Si1 that is BDA in the terminal fragment model FS1 is bonded to another fragment model (a non-terminal fragment model) (an arrow of a solid line in FIG. 17), and these fragment models form new one fragment model FN1. In another bonding form, O4 that is BAA in the terminal fragment model FS1 is bonded to another fragment model (an arrow of a broken line in FIG. 17), and these fragment models form new one fragment model FN2.

Figure 18:
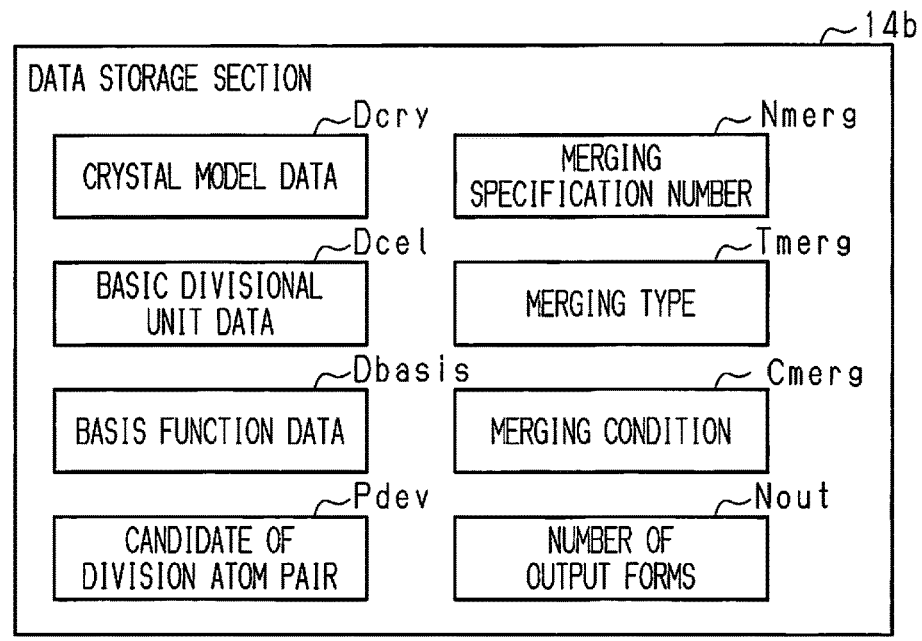
FIG. 18 is a diagram illustrating types of data to be stored in the storage device according to the second embodiment.

As shown in FIG. 18, the crystal model data Dcry, the basic divisional unit data Dcel, the division atom pair candidate Pdev, a merging specification number Nmerg, a merging type Tmerg, a merging condition Cmerg, the basis function data Dbasis, and the number of output forms Nout are stored in the data storage section 14b. These data are input from the input device 12.

The merging specification number Nmerg represents the number of atoms of a fragment model that is a threshold representing whether the merging process is automatically executed. For example, when the merging specification number Nmerg is 3, a fragment model, such as an OH fragment model, in which the number of atoms is less than three is selected as a target that undergoes the automatic merging process. BDA or BAA included in the fragment model in which the number of atoms is less than three is treated as being bonded to another fragment model adjacent to the fragment model, and an atom group including the atoms of both the fragment models is created as new one fragment model.

The merging type Tmerg represents a fragment model that undergoes the merging process, and the format of the merging process to be applied to the fragment model. For example, first, second and third formats are set in the type numbers N of the terminal fragment models FS1, FS2 and FS3, respectively.

The merging condition Cmerg represents an atom to be a bonding source in a target for the merging process, namely, BDA or BAA. The merging condition Cmerg represents an atom of the bonding source for each format represented by the merging type Tmerg. For example, in the first format, BDA in the terminal fragment model FS1 is bonded to BAA in another fragment model adjacent to the BDA. In the second format, BDA in the terminal fragment model FS2 is bonded to BAA in another fragment model adjacent to the BDA. In the third format, BDA in the terminal fragment model FS3 is bonded to BAA in another fragment model adjacent to the BDA.

In the merging condition Cmerg, atoms of a plurality of different bonding sources may be alternatively shown for one format represented by the merging type Tmerg. For example, in the first format, a format in which BDA in the terminal fragment model FS1 is bonded to another fragment model, and a format in which BAA in the terminal fragment model FS1 is bonded to another fragment model may be alternatively shown.

The control device 11 will be described with reference to FIG. 19.

Figure 19:
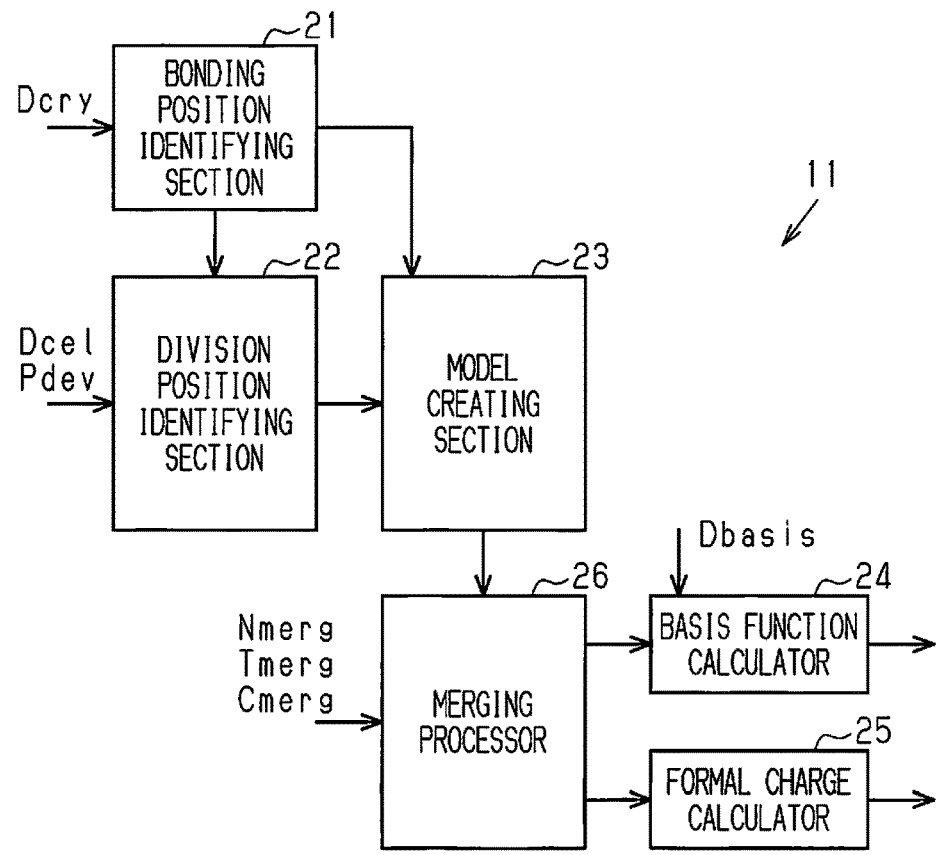
FIG. 19 is a block diagram functionally illustrating the control device according to the second embodiment.

As shown in FIG. 19, the control device 11 has a merging processor 26. The merging processor 26 extracts a fragment model that automatically undergoes the merging process by using model data that is the output result from the model creating section 23 and the merging specification number Nmerg. For example, the merging processor 26 calculates the number of atoms in each of the fragment models for each fragment model, and extracts fragment models in which the number of the atoms is less than the merging specification number Nmerg as targets that automatically undergo the merging process. The merging processor 26 treats BDA or BAA of the extracted fragment model as being bonded to another fragment model adjacent to the BDA or the BAA, and corrects these two fragment models into one fragment model.

The merging processor 26 executes the merging process on each target for the merging process represented by the merging condition Cmerg by using the model data that is the output result from the model creating section 23, the merging type Tmerg, and the merging condition Cmerg in a format represented by the merging type Tmerg.

For example, the merging processor 26 treats BDA in the terminal fragment model FS1 as being bonded to BAA in the non-terminal fragment model adjacent to the BDA according to the first format of the merging type Tmerg, and corrects these two fragment models into one fragment model in the merging data. Similarly, the merging processor 26 treats BDA in the terminal fragment model FS2 as being bonded to BAA in the non-terminal fragment model adjacent to the BDA according to the second format, and corrects these two fragment models. into one fragment model in the merging data. Further, the merging processor 26 treats BDA in the terminal fragment model FS3 as being bonded to BAA in the non-terminal fragment model adjacent to the BDA according to the third format, and corrects these two fragment models into one fragment model in the merging data. The merging processor 26 functions as an output section and generates model data in which each of the constituent atoms of the crystal model is associated with the corrected fragment model including each of the constituent atoms, and outputs the model data to the basis function calculator 24 and the formal charge calculator 25.

The basis function calculator 24 calculates the number of the basis functions necessary for the fragment models by using the model data as the output result from the merging processor 26 and the basis function data Dbasis, and outputs the calculated result to the output device 13. Further, the formal charge calculator 25 calculates the formal charges of the fragment models by using the model data as the output result from the merging processor 26 and the number of electrons of each atom, and outputs the calculated result to the output device 13.

The output device 13 outputs a division result in each division form of the crystal model as to each of the fragment models created by the control device 11 similarly to the first embodiment. Further, the output device 13 outputs data in which the division results created by the control device 11 is associated with evaluated values of the division results, as the evaluation results. Further, the output device 13 outputs data about the charge state of the fragment model for each of new fragment models created by the merging process as a result of the merging process.

FIG. 20 illustrates one example of a display view of the merging type Tmerg and the merging condition Cmerg displayed by the output device 13, and FIG. 21 illustrates one example of the result of the merging process displayed by the output device 13.

As shown in FIG. 20, for example, "2", "3", and "7", which are the type numbers N to be associated with the first, second and third formats, are displayed on a display view VMcon of the merging type Tmerg and the merging condition Cmerg. Further, an asterisk (*) indicates that the atom corresponding to BDA in the first format is Si1 on the display view VMcon, and is bonded to BAA in another fragment model adjacent to the BDA. Further, an asterisk (*) indicates that the atom corresponding to BDA in the first format is O4, and is bonded to BAA in another fragment model adjacent to the BDA. That is, atoms of a plurality of different bonding sources are alternatively shown on the display view VMcon for one format represented by the merging type Tmerg.

As shown in FIG. 21, model data applied to the merging process is displayed as Dif on a display view VMeva of the result of the merging process. For example, when the output result from the model creating section 23 is applied to the merging process, a file including that model data is indicated as "SIO_UC_STEP 1".

For example, combination numbers Nmtype to be allocated to the formats of the merging process are associated with the following four entries on the display view VMeva of the result of the merging process.

A combination of the processing formats Comb
A formal charge of the crystal model Ncs
A maximum number Amax of atoms included in the fragment model
The number of the basis functions Nbs necessary for the crystal model The combination Comb is a specific bit value representing the combination of the formats of the merging process, and is uniquely determined based on the merging type Tmerg and the merging condition Cmerg. For example, as shown in FIG. 21, when the merging type Tmerg is the first to third formats, the combination Comb is indicated by three bits. As shown in FIG. 21, when atoms of different two bonding sources are determined for each of the first to third formats, each bit of the combination Comb is indicated by "0" or "1".

Concretely, the combination Comb "000" is associated with the merging process corresponding to the combination number Nmtype "1", and Si1, Si2, and O1 are set as BDA of the first, second and third formats, respectively. The combination Comb "001" is associated with the merging process corresponding to a format number Nmtype "2", O4, Si2, and O1 are set as BDA of the first, second and third formats, respectively. The combination Comb "010" is associated with the merging process corresponding to the format number Nmtype "3", Si1, O6, and O1 are set as BDA of the first, second and third formats, respectively.

Figure 22:
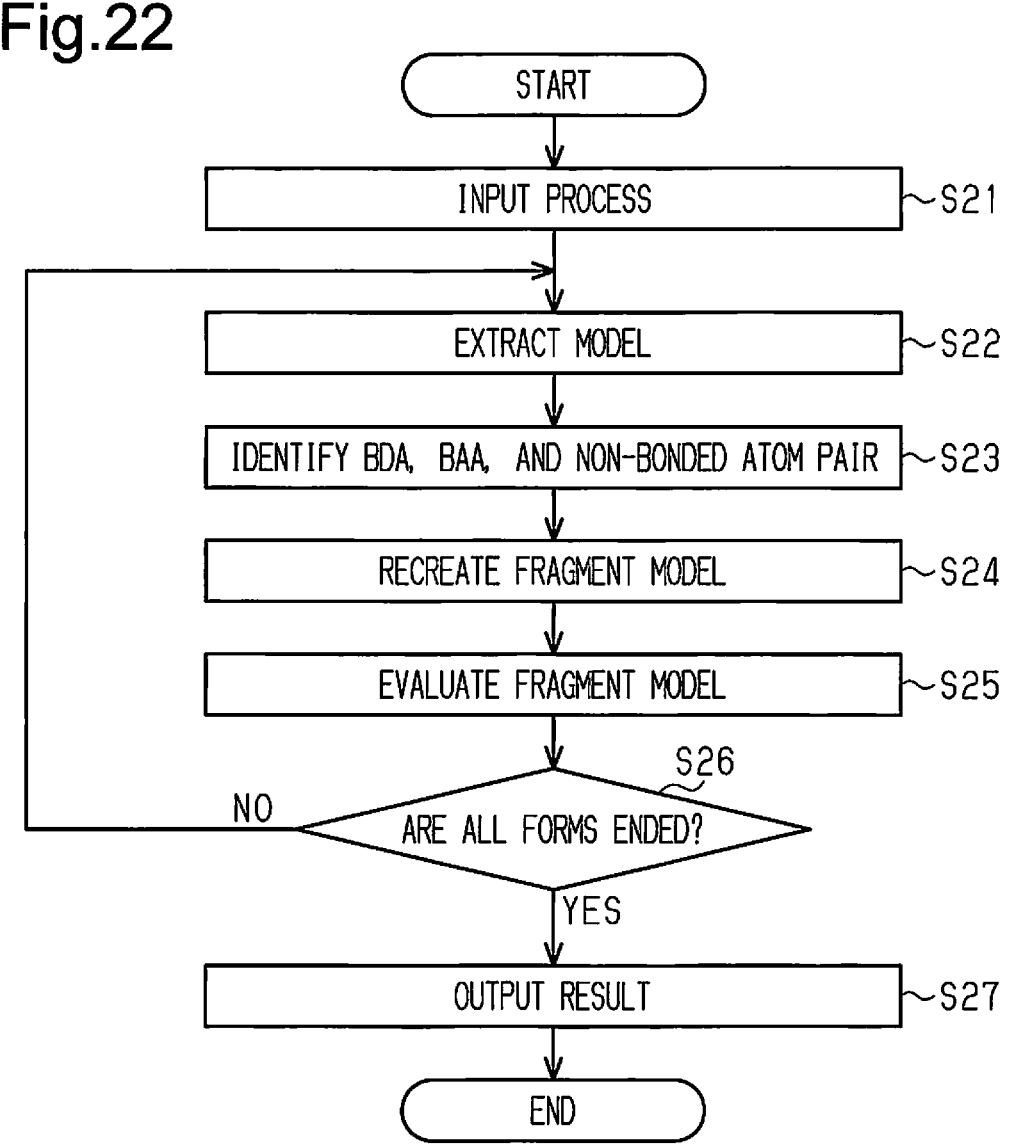
FIG. 22 is a flowchart illustrating a procedure of the merging process in the second embodiment.

The fragment model creating method that is executed by the fragment model creating system will now be described with reference to FIG. 22. The merging process in the fragment model creating method that is executed by using the merging type Tmerg and the merging condition Cmerg will be described below.

Model data that undergoes the merging process is input into the merging processor 26 (the control device 11) from the model creating section 23 or the storage device 14. Further, the merging type Tmerg and the merging condition Cmerg are input into the merging processor 26 from the storage device 14 (step S21).

The merging processor 26 extracts a fragment model to be merged by using the model data, the merging type Tmerg, and the merging condition Cmerg. The control device 11 extracts the fragment model to be merged and a fragment model that is a bonding destination (step S22). The merging processor 26 identifies BDA and BAA for the extracted fragment model by using the extracted fragment model and the merging condition Cmerg (step S23). The merging processor 26 creates a new fragment model composed of the fragment model including the identified BDA and the fragment model including the identified BAA, and updates the model data (step S24).

The control device 11 calculates the total sum of the absolute values of the formal charge in each fragment model created by the merging processor 26, and the number of the basis functions necessary for the respective fragment models (step S25). The control device 11 determines whether the merging process has been executed on all the combinations of the atoms of the bonding sources represented by the merging condition Cmerg (step S26).

When the merging process has not been executed on all the combinations of the atoms of the bonding sources represented by the merging condition Cmerg ("NO" at step S26), the control device 11 repeats step S22 to step S26 on another format in which the merging process has not been executed.

When the merging process has been executed on all the combinations of the atoms of the bonding sources represented by the merging condition Cmerg ("YES" at step S26), the control device 11 assigns priorities to all the combinations of the atoms of the bonding sources in the ascending order of the total sum of the absolute values of the formal charges in the fragment model. At this time, priorities are assigned to the combinations having the same total sum of the absolute values of the formal charges in the ascending order of the maximum value of the size of the fragment model included in each combination, namely, the maximum value of the number of the basis functions necessary for the fragment model. The control device 11 outputs the division result and the evaluation result from the output device 13 with reference to the assigned priorities (step S27).

The second embodiment achieves the following advantages.

(7) The merging processor 26 cancels setting of the division of some division atom pairs among the division atom pairs of a plurality of BDAs and a plurality of BAAs identified by the division position identifying section 22. The merging processor 26 converts the adjacent two fragment models including the canceled the division atom pairs into one fragment model. For this reason, the size of the once created fragment model and the types of the constituent atoms of the fragment model can be changed.

(8) In the merging processor 26, a plurality of different formats is set as the formats of the merging process, so that the merging process is executed for each of the formats. The output device 13 creates the fragment model according to each format of the merging process. For this reason, the diversity of the fragment model created by the merging process can be heightened.

(9) The formal charge Ncs of the crystal model, the maximum value Amax of the number of atoms included in the fragment model, the number of the basis functions Nbs necessary for the crystal model are displayed on the display view VMeva of the result of the merging process according to each format of the merging process. For this reason, the user can understand the evaluated value of the fragment model according to each format of the merging process.

The above illustrated embodiments may be modified as follows.

The control device 11 in the first embodiment may execute only the automatic merging process in the functions of the merging processor 26 in the second embodiment.

The control device 11 may have a polarization calculator for calculating a polarization of the formal charge in the crystal model by using the calculated result of the formal charge calculator 25. Not only the formal charge of the crystal model but also a polarization of the formal charge in the crystal model may be set as the evaluated value to be used for the evaluation result.

In FIGS. 11 to 13, white is associated with the fragment model having the standard formal charge and size, and as the formal charge and the size deviate further from the standards, colors closer to black are associated with the fragment model.

Not limited to this, when the formal charge is represented by a corresponding color, white may be associated with the formal charge that is a standard. When the formal charge of the fragment model is larger than the standard in the positive direction, one color such as red may be associated with the fragment model. When the formal charge of the fragment model is larger than the standard in the negative direction (namely, smaller than the standard), another color such as blue may be associated with the fragment model. In this case, it is preferable that as the formal charge of the fragment model approaches the maximum value in the positive direction and as the formal charge approaches the maximum value in the negative direction (namely, the minimum value), a color with higher chroma be associated with the fragment model.

Further, when each size is represented by a corresponding color, white may be associated with the standard size. When the size of the fragment model is larger than the standard, one color such as red may be associated with the fragment model. When the size is smaller than the standard, another color such as blue may be associated with the fragment model. In this case, similarly to the case of the formal charge, it is preferable that colors with different chroma be associated with the fragment model according to the difference between the size of the fragment model and the standard size.

The control device 11 may calculate the formal charge and a polarization of the formal charge for each layer in the crystal model composed of a plurality of layers, and the output device 13 may indicate the formal charge shown in FIGS. 11 to 13 for each layer, for example. Such information about the charge state for each layer in the crystal model is useful for an analysis of the interaction energy between a surface of the crystal model and another compound model, such as an analysis of the interaction energy between a peptide model and a crystal model.

The control device 11 may have a size calculator for calculating the size of a fragment model by using the constituent atoms of the fragment model and the coordinates of the constituent atoms. The maximum value in each size of each of the fragment models may be set as the evaluated value used for the evaluation result.

The evaluated value used for the evaluation result may be any two or more of the total sum of the absolute values of the formal charges in the crystal model, the polarization of the formal charge of each fragment model in the crystal model, and the maximum value of the size in each of the fragment models.

The division result Dresl of each candidate Dcand in each division atom pair is associated with each candidate Dcand of each division atom pair so as to be displayed on the display view Veva, which displays the evaluation result. Not limited to this, the candidate Dcand of the division atom pair may be simply associated with the evaluated value Pseq so as to be displayed on the display view Veva, which displays the evaluation result.

The bonded pair for identifying BDA and BAA may be identified in the crystal model data Dcry in advance. In this case, the bonding position identifying section 21 can be omitted from the control device 11.

The creation of the terminal fragment models FS1, FS2 and FS3 depends on the constituent atoms of the crystal model and the constituent atoms of the basic divisional unit. For this reason, the terminal fragment models FS1, FS2 and FS3 do not have to be created. That is, any modification may be made as long as the crystal model is divided into a plurality of basic divisional units and each candidate included in each of the basic divisional units are identified as a division atom pair.

BDA and BAA do not have to be included in the division result. In short, any modification may be made as long as the fragment model is created by candidate atoms in each unit model.

The storage device 14 stores an atom group included in the crystal lattice according to each type of crystal, and the control device 11 may use the atom group included in the crystal lattice as the basic divisional unit. That is, the basic divisional unit may be determined for each crystal model in advance.

When interaction energy between the above nonmetallic crystal and a biological macromolecule, such as a protein of various enzyme or DNA and RNA, which are nucleic acid, is calculated by the FMO method, the fragment model created by the method described in the above embodiment can be used. When the crystal model is divided into the fragment models, distribution of the formal charge and the size of the fragment model composing each surface of the crystal model often varies depending on the surfaces of the crystal model.

When the above interaction is calculated by the FMO method, it is preferable that the sizes of the respective fragment models composing a surface that interacts with a biological macromolecule, namely, an absorption surface be equal to the size of the basic divisional unit. Further, it is preferable that the formal charges of the respective fragment models composing the absorption surface be ±0.

For this reason, as shown in FIGS. 11 to 13, when colors are associated with the respective fragment models composing the molecular structure Vstr displayed on the display view Veva according to the formal charge and the size, the surface composed of the fragment models with white is preferable as the absorption surface. That is, when the molecular structure Vstr is displayed with colors being associated with the fragment models, a surface that should be set as the absorption surface in the crystal model can be easily selected.

Not only the nonmetallic crystal is an object of the crystal model, and in addition to the nonmetallic crystal, a complex including at least one of water molecule, DNA, ion, peptide and protein may be used. In this case, a complex of the nonmetallic crystal and another molecule is treated as one crystal model, so that a fragment model is created for the crystal model. For this reason, when the complex is treated as one crystal model, a fragment model including both atoms composing the nonmetallic crystal and atoms forming another molecule can be created on a boundary between the nonmetallic crystal and another molecule.

In the fragment model creating system, different input devices 12 may be connected to one control device 11 via a network. One control device 11 may create fragment models individually by using input data from the different input devices 12. The control device 11 may have at least one of the function of the storage device 14 and the function of the output device 13.

The invention claimed is:

1. A three-dimensional fragment model creating device for creating and visualizing a plurality of different three-dimensional fragment models from a nonmetallic crystal model, comprising:
   a controller configured to receive input data and use the input data to create the plurality of different three-dimensional fragment models, each of the different three-dimensional fragment models representing a different, basic divisional unit of the nonmetallic crystal, a plurality of which together model the nonmetallic crystal in three dimensions, the controller including:
      a division position identifying control portion adapted for identifying a plurality of division atom pairs for a plurality of atoms included in the nonmetallic crystal model, the atoms in the division atom pairs being included in the plurality of different three-dimensional fragment models;
      a model creating control portion adapted for identifying each of a plurality of atom groups composed of atoms bonded to each other in the nonmetallic crystal model to create the plurality of different three-dimensional fragment models corresponding to the respective identified atom groups;
   an input device connected to, and in communication with, the controller, the input device configured to transmit the input data to the controller;
   a storage device connected to, and in communication with, the controller, the storage device configured to store data, including the input data and the identified plurality of division atom pairs, and
   an output device in communication with, and controlled by the controller;
   wherein:
   each of the plurality of different three-dimensional fragment models is set as a corresponding basic divisional unit,
   each of the atoms included in the nonmetallic crystal model is associated with any one of the atoms included in the basic divisional unit,
   the division position identifying control portion is also adapted for setting candidates of the division atom pairs in the atoms included in the basic divisional units, and identifying the candidates included in each basic divisional unit as the division atom pairs, the candidates comprising identified bond detached atom (BDA) candidates and bond attached (BAA) candidates that have been three-dimensionally scattered so as to be complicatedly distributed in the nonmetallic crystal model,
   the output device is adapted for outputting a visual indication of each of the plurality of different three-dimensional fragment models to a user, the visual indication including an indication of a characteristic of each of the different three-dimensional fragment models and candidates of the division atom pairs.

2. The three-dimensional fragment model creating device according to claim 1, wherein the output device is adapted to output the identified division atom pairs for the respective three-dimensional fragment models.

3. The three-dimensional fragment model creating device according to claim 2, further comprising a merging processor adapted for canceling the setting of division of some of the division atom pairs and for converting two adjacent three-dimensional fragment models including the canceled division atom pairs into one three-dimensional fragment model.

4. The three-dimensional fragment model creating device according to claim 1, wherein:
   the division position identifying control portion is further adapted for setting the candidates that are different from each other and for identifying the division atom pair for each of the candidates, and
   the model creating control portion is further adapted for creating the three-dimensional fragment model by using the division atom pair identified for each of the candidates.

5. The three-dimensional fragment model creating device according to claim 4, wherein
   the model creating control portion is adapted for calculating an evaluated value of the three-dimensional fragment model for each candidate, and
   the output device is adapted for outputting the candidates in correspondence with the evaluated values.

6. The three-dimensional fragment model creating device according to claim 5, wherein the evaluated value is at least one of a total sum of absolute values of formal charges in the nonmetallic crystal model, polarization of the formal charges in the nonmetallic crystal model, and a maximum value of sizes of the three-dimensional fragment models.

7. The three-dimensional fragment model creating device according to claim 5, wherein the output device is further adapted for indicating at least one of formal charges in the three-dimensional fragment models and sizes of the three-dimensional fragment models by using visual indicators that are colors corresponding to different elements.

8. A three-dimensional fragment model creating system for creating and visualizing a plurality of different three-dimensional fragment models from a nonmetallic crystal model, comprising:
   an input device configured to receive input data; and
   a three-dimensional fragment model creating device for creating and visualizing a plurality of different three-dimensional fragment models by using data input from the input device, wherein
   the three-dimensional fragment model creating device includes:
      a controller connected to the input device and configured to receive the input data transmitted from the input device, the controller configured to create the plurality of different three-dimensional fragment models using the input data received from the input device, each of the different three-dimensional fragment models representing a different, basic divisional unit of the nonmetallic crystal, a plurality of which together model the nonmetallic crystal in three dimensions, the controller including:
         a division position identifying control portion adapted for identifying a plurality of division atom pairs for a plurality of atoms included in the nonmetallic crystal model, the atoms in the division atom pairs being included in the plurality of different three-dimensional fragment models;

a model creating control portion adapted for identifying each of a plurality of atom groups composed of atoms bonded to each other in the nonmetallic crystal model to create the plurality of different three-dimensional fragment models corresponding to the respective identified atom groups;

a storage device connected to, and in communication with, the controller, the storage device configured to store data, including the input data and the identified plurality of division atom pairs, and an output device in communication with, and controlled by the controller;

wherein:

each of the plurality of different three-dimensional fragment models is set as a corresponding basic divisional unit, each of the atoms included in the nonmetallic crystal model is associated with any one of the atoms included in the basic divisional unit, the division position identifying control portion is also adapted for setting candidates of the division atom pairs in the atoms included in the basic divisional units, and identifying the candidates included in each basic divisional unit as the division atom pairs, the candidates comprising identified bond detached atom (BDA) candidates and bond attached (BAA) candidates that have been three-dimensionally scattered so as to be complicatedly distributed in the nonmetallic crystal model, and the output device is adapted for outputting a visual indication of each of the plurality of different three-dimensional fragment models to a user, the visual indication including an indication of a characteristic of each of the different three-dimensional fragment models and candidates of the division atom pairs.

9. A three-dimensional fragment model creating and visualizing method for creating and visualizing a plurality of different three-dimensional fragment models from a nonmetallic crystal model, comprising:

receiving input data at an input device, transmitting the input data from the input device to a controller configured to create a three-dimensional fragment model, identifying, using a division position identifying control portion of the controller, a plurality of division atom pairs for a plurality of atoms included in the nonmetallic crystal model, the atoms in the division atom pairs being included in the plurality of different three-dimensional fragment models; and identifying, using a model creating control portion of the controller, each of a plurality of atom groups composed of atoms bonded to each other in the nonmetallic crystal model to create the plurality of different three-dimensional fragment models corresponding to the respective identified atom groups, wherein each of the plurality of different three-dimensional fragment models is set as a corresponding basic divisional unit, each of the atoms included in the nonmetallic crystal model is associated with any one of the atoms included in the basic divisional unit, the identification of the division atom pairs includes:

setting candidates of the division atom pairs in the atoms included in the basic divisional units, the candidates comprising identified bond detached atom (BDA) candidates and bond attached (BAA) candidates that have been three-dimensionally scattered so as to be complicatedly distributed in the nonmetallic crystal model, and identifying the candidates included in each basic divisional units as the division atom pairs, storing the input data and division atom pairs in a storage device accessible to the controller, and outputting a visual indication of each of the plurality of different three-dimensional fragment models to a user, the visual indication including an indication of a characteristic of each of the different three-dimensional fragment models and candidates of the division atom pairs.

10. A non-transitory computer readable recording medium recording therein a program for creating and visualizing a three-dimensional fragment model by using the three-dimensional fragment model creating system for creating a three-dimensional fragment model according to the method of claim 9.

11. The device of claim 1, wherein the output device is adapted for outputting a visual indicator that is a color that indicates a size of one of the different three-dimensional fragment models, and for outputting another visual indicator that is another color that indicates another size of another one of the different three-dimensional fragment models, such that a relative size comparison of two three-dimensional fragment models is visually available to a user.

12. The device of claim 1, wherein the output device is adapted for outputting a visual indicator that is a color that indicates a charge state of one of the different three-dimensional fragment models, and for outputting another visual indicator that is another color that indicates another charge state of another one of the different three-dimensional fragment models, such that a relative charge state comparison of two three-dimensional fragment models is visually available to a user.

13. The device of claim 1, wherein the output device is adapted for outputting a visual indicator that indicates that one atom of a division atom pair is a bond detached atom (BDA) and another visual indicator that indicates that another atom of a division atom pair is a bond attached atom (BAA).

14. The device of claim 13, wherein the visual indicator for the BDA is a colon (:) and the visual indicator for the BAA is a dash (-).

15. The device of claim 1, wherein the characteristic is one of a charge state of a three-dimensional fragment model and a size of a three-dimensional fragment model.

16. A three-dimensional fragment model creating device comprising:

circuitry configured to:

create a plurality of different three-dimensional fragment models, each of the different three-dimensional fragment models representing a different, basic divisional unit of a nonmetallic crystal, a plurality of which together model the nonmetallic crystal;

identify a plurality of division atom pairs for a plurality of atoms included in the nonmetallic crystal model, the atoms in the division atom pairs being included in the plurality of different three-dimensional fragment models;

identify each of a plurality of atom groups composed of atoms bonded to each other in the nonmetallic crystal model;

create the plurality of different three-dimensional fragment models corresponding to the respective identified atom groups;

set each of the plurality of different three-dimensional fragment models as a corresponding basic divisional unit;

associate each of the atoms included in the nonmetallic crystal model with any one of the atoms included in the basic divisional unit;

set candidates of the division atom pairs in the atoms included in the basic divisional units the candidates comprising identified bond detached atom (BDA) candidates and bond attached (BAA) candidates that have been three-dimensionally scattered so as to be complicatedly distributed in the nonmetallic crystal model, identify the candidates included in each basic divisional unit as the division atom pairs; and output a visual indication of each of the plurality of different three-dimensional fragment models to a user, the visual indication including an indication of a characteristic of each of the different three-dimensional fragment models and candidates of the division atom pairs.

17. The three-dimensional fragment model creating device according to claim 16, wherein the circuit is further configured to:

calculate an evaluated value of the three-dimensional fragment model for each of the candidates of the division atom pairs, wherein the evaluated value is at least one of a total sum of absolute values of formal charges in the nonmetallic crystal model, polarization of the formal charges in the nonmetallic crystal model, and a maximum value of sizes of the three-dimensional fragment models; and output a division result that includes a coordinate list representing coordinates of constituent atoms included in the three-dimensional fragment model, and a charge state list representing charge states of the three-dimensional fragment models for each of division forms of the nonmetallic crystal model, and the evaluated values correlated to the division results.

18. The three-dimensional fragment model creating device according to claim 16, wherein the circuit is further configured to:

assign constituent atoms of the nonmetallic crystal model to any of the constituent atoms in a basic divisional unit, where the basic divisional unit is a three-dimensional unit atom group that is repeated in the nonmetallic crystal model;

extract the constituent atoms corresponding to candidates of division atom pairs for each of the basic divisional units as candidates of bond detached atoms and bond attached atoms, wherein a division atom pair candidate is a combination of one or more atoms set as candidates of the bond detached atoms and one or more atoms set as candidates of the bond attached atoms in the constituent atoms of the basic divisional unit;

identify a combination of the bond detached atoms and the bond attached atoms included in bonded pairs by using data representing the bonded pairs, wherein the data is generated by calculation of an interatomic distance, the interatomic distance is a distance between two different atoms in an atom pair for all the constituent atoms in the nonmetallic crystal model, the bonded pair is the atom pair in which both atoms are bonded; and identify a non-bonding atom pair that is not included in the bonded pair, wherein the non-boning atom pair is the atom pair in which the atoms are not bonded.

19. The three-dimensional fragment model creating device according to claim 18, wherein the circuit is further configured to:

correct the bonded pair by excluding the bond detached atoms, the bond attached atoms, and the non-bonded atom pair from the bonded pair;

identify each of atom groups in which the corrected bonded pairs are connected in the constituent atoms of the nonmetallic crystal model; and create each of the three-dimensional fragment models correspond to each of the identified atom groups.

* * * * *